US012653667B2

(12) United States Patent
Levi et al.

(10) Patent No.: US 12,653,667 B2
(45) Date of Patent: Jun. 16, 2026

(54) PROSTHETIC HEART VALVE LEAFLET ASSEMBLIES AND METHODS

(71) Applicant: EDWARDS LIFESCIENCES CORPORATION, Irvine, CA (US)

(72) Inventors: Tamir S. Levi, Zikhron Yaakov (IL); Shahram Zamani, Newport Coast, CA (US); Michael Bukin, Pardes Hanna (IL); Ziv Yohanan, Kfar Hahoresh (IL); Noam Nir, Pardes-Hanna (IL); Tyler Dale O'Dell, Irvine, CA (US); Elena Sherman, Pardes Hana (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 18/920,663

(22) Filed: Oct. 18, 2024

(65) Prior Publication Data

US 2025/0041053 A1 Feb. 6, 2025

Related U.S. Application Data

(60) Division of application No. 18/195,288, filed on May 9, 2023, now Pat. No. 12,232,956, which is a
(Continued)

(51) Int. Cl.
*A61F 2/24* (2006.01)

(52) U.S. Cl.
CPC .......... *A61F 2/2415* (2013.01); *A61F 2/2418* (2013.01); *A61F 2220/0075* (2013.01)

(58) Field of Classification Search
CPC .... A61F 2/2415; A61F 2/2418; A61F 2/2439; A61F 2220/0091; A61F 2220/0075
See application file for complete search history.

(56) References Cited

U.S. PATENT DOCUMENTS 3,409,013 A 11/1968 Henry
3,548,417 A * 12/1970 Kischer ............... F16K 15/1471
137/844
(Continued)

FOREIGN PATENT DOCUMENTS

AU 2020233732 A1 10/2020
AU 2020233732 B2 * 5/2022 ........... A61F 2/2418
(Continued)

OTHER PUBLICATIONS

Andersen, H.R. "History of Percutaneous Aortic Valve Prosthesis," Herz No. 34. pp. 343-346. 2009.
(Continued)

*Primary Examiner* — Bayan Salone
(74) *Attorney, Agent, or Firm* — Klarquist Sparkman, LLP

(57) ABSTRACT

A method of assembling a valvular structure can include folding an upper tab of a first leaflet onto a lower tab of the first leaflet, disposing a first end of a reinforcing member on the upper tab, disposing a commissure member adjacent the lower tab, and coupling the first end of the reinforcing member, the tabs of the first leaflet, and the commissure member to one another. The method can further include folding an upper tab of a second leaflet onto a lower tab of the second leaflet, disposing the second leaflet adjacent the first leaflet such that the commissure member is positioned between the lower tabs, disposing a second end of the reinforcing member on the upper tab of the second leaflet, and coupling the reinforcing member, the upper and lower tabs of the second leaflet, and the commissure member to one another to form a commissure.

14 Claims, 14 Drawing Sheets

Related U.S. Application Data continuation of application No. PCT/US2021/058918, filed on Nov. 11, 2021.

(60) Provisional application No. 63/113,034, filed on Nov. 12, 2020.

(56) References Cited

U.S. PATENT DOCUMENTS

| | | | | |
|---|---|---|---|---|
| 3,587,115 A | * | 6/1971 | Shiley | A61F 2/2427 623/2.38 |
| 3,657,744 A | | 4/1972 | Ersek | |
| 3,671,979 A | | 6/1972 | Moulopoulos | |
| 3,714,671 A | * | 2/1973 | Edwards | A61F 2/2418 623/2.19 |
| 3,755,823 A | * | 9/1973 | Hancock | A61F 2/2418 623/2.18 |
| 3,983,581 A | * | 10/1976 | Angell | A61F 2/2409 623/2.15 |
| 4,035,849 A | * | 7/1977 | Angell | A61F 2/2409 264/222 |
| 4,056,854 A | | 11/1977 | Boretos et al. | |
| 4,106,129 A | | 8/1978 | Carpentier et al. | |
| 4,222,126 A | * | 9/1980 | Boretos | A61F 2/2412 137/849 |
| 4,265,694 A | * | 5/1981 | Boretos | A61F 2/2412 623/901 |
| 4,297,749 A | | 11/1981 | Davis et al. | |
| 4,339,831 A | | 7/1982 | Johnson | |
| 4,343,048 A | | 8/1982 | Ross et al. | |
| 4,345,340 A | | 8/1982 | Rosen | |
| 4,373,216 A | | 2/1983 | Klawitter | |
| 4,406,022 A | * | 9/1983 | Roy | A61F 2/2403 137/527 |
| 4,441,216 A | * | 4/1984 | Ionescu | A61F 2/2418 623/2.19 |
| 4,470,157 A | * | 9/1984 | Love | A61F 2/2412 623/2.15 |
| 4,535,483 A | | 8/1985 | Klawitter et al. | |
| 4,574,803 A | | 3/1986 | Storz | |
| 4,592,340 A | * | 6/1986 | Boyles | A61M 25/1002 604/247 |
| 4,605,407 A | * | 8/1986 | Black | A61F 2/2418 623/2.17 |
| 4,612,011 A | * | 9/1986 | Kautzky | A61K 35/30 623/2.1 |
| 4,643,732 A | * | 2/1987 | Pietsch | A61F 2/2412 623/2.2 |
| 4,655,771 A | * | 4/1987 | Wallsten | A61F 2/958 606/198 |
| 4,692,164 A | * | 9/1987 | Dzemeshkevich | A61F 2/2412 623/2.14 |
| 4,733,665 A | * | 3/1988 | Palmaz | A61F 2/915 606/191 |
| 4,759,758 A | * | 7/1988 | Gabbay | A61F 2/2412 623/2.13 |
| 4,762,128 A | * | 8/1988 | Rosenbluth | A61F 2/958 604/103.08 |
| 4,777,951 A | | 10/1988 | Cribier et al. | |
| 4,787,899 A | | 11/1988 | Lazarus | |
| 4,787,901 A | * | 11/1988 | Baykut | A61F 2/2412 623/1.26 |
| 4,796,629 A | * | 1/1989 | Grayzel | A61M 25/104 604/103.09 |
| 4,820,299 A | * | 4/1989 | Philippe | A61F 2/2409 623/2.23 |
| 4,829,990 A | * | 5/1989 | Thuroff | A61F 2/26 600/40 |
| 4,851,001 A | * | 7/1989 | Taheri | A61F 2/2403 623/1.24 |
| 4,856,516 A | * | 8/1989 | Hillstead | A61F 2/88 606/1 |

| | | | | |
|---|---|---|---|---|
| 4,878,495 A | * | 11/1989 | Grayzel | A61M 25/1011 606/193 |
| 4,878,906 A | * | 11/1989 | Lindemann | A61F 2/958 623/3.18 |
| 4,883,458 A | * | 11/1989 | Shiber | A61B 8/12 606/159 |
| 4,922,905 A | * | 5/1990 | Strecker | A61F 2/2424 606/195 |
| 4,966,604 A | * | 10/1990 | Reiss | A61B 17/320725 606/159 |
| 4,979,939 A | * | 12/1990 | Shiber | A61B 17/320758 606/159 |
| 4,986,830 A | * | 1/1991 | Owens | A61M 29/02 604/96.01 |
| 4,994,077 A | | 2/1991 | Dobben | |
| 5,007,896 A | * | 4/1991 | Shiber | A61B 18/245 606/159 |
| 5,026,366 A | * | 6/1991 | Leckrone | A61B 18/28 606/7 |
| 5,032,128 A | * | 7/1991 | Alonso | A61F 2/2409 623/2.4 |
| 5,037,434 A | * | 8/1991 | Lane | A61F 2/2418 623/2.18 |
| 5,047,041 A | | 9/1991 | Samuels | |
| 5,059,177 A | | 10/1991 | Towne et al. | |
| 5,080,668 A | * | 1/1992 | Bolz | A61L 27/50 623/2.28 |
| 5,085,635 A | * | 2/1992 | Cragg | A61M 25/007 604/102.03 |
| 5,089,015 A | * | 2/1992 | Ross | A61F 2/2427 606/144 |
| 5,152,771 A | * | 10/1992 | Sabbaghian | A61B 17/32075 606/198 |
| 5,163,953 A | * | 11/1992 | Vince | A61F 2/2418 623/2.11 |
| 5,167,628 A | * | 12/1992 | Boyles | A61M 25/1002 604/103.1 |
| 5,192,297 A | * | 3/1993 | Hull | A61F 2/06 604/103.05 |
| 5,258,023 A | * | 11/1993 | Reger | A61F 2/2412 623/2.18 |
| 5,266,073 A | | 11/1993 | Wall | |
| 5,282,847 A | * | 2/1994 | Trescony | A61F 2/06 623/1.49 |
| 5,295,958 A | * | 3/1994 | Shturman | A61B 18/1492 606/159 |
| 5,332,402 A | * | 7/1994 | Teitelbaum | A61F 2/2424 623/2.35 |
| 5,360,444 A | * | 11/1994 | Kusuhara | A61F 2/2454 623/900 |
| 5,370,685 A | * | 12/1994 | Stevens | A61M 25/10 623/2.11 |
| 5,397,351 A | * | 3/1995 | Pavcnik | A61F 2/2409 623/2.35 |
| 5,411,055 A | * | 5/1995 | Kane | F16K 47/10 137/513.5 |
| 5,411,552 A | * | 5/1995 | Andersen | A61F 2/2475 137/844 |
| 5,443,446 A | * | 8/1995 | Shturman | A61M 60/896 128/898 |
| 5,480,424 A | * | 1/1996 | Cox | A61F 2/2412 623/2.15 |
| 5,500,014 A | * | 3/1996 | Quijano | A61F 2/2418 623/1.24 |
| 5,545,209 A | * | 8/1996 | Roberts | A61M 25/10 604/103.05 |
| 5,549,665 A | * | 8/1996 | Vesely | A61F 2/2409 623/2.14 |
| 5,554,185 A | * | 9/1996 | Block | A61F 2/2412 623/2.12 |
| 5,558,644 A | * | 9/1996 | Boyd | A61M 25/0152 604/102.02 |
| 5,571,175 A | * | 11/1996 | Vanney | A61F 2/2409 623/2.41 |
| 5,584,803 A | | 12/1996 | Stevens et al. | |

(56) References Cited

U.S. PATENT DOCUMENTS

| | | | | |
|---|---|---|---|---|
| 5,591,185 | A * | 1/1997 | Kilmer | A61F 9/013 |
| | | | | 606/166 |
| 5,591,195 | A | 1/1997 | Taheri et al. | |
| 5,607,464 | A * | 3/1997 | Trescony | A61F 2/06 |
| | | | | 623/1.29 |
| 5,609,626 | A * | 3/1997 | Quijano | A61F 2/062 |
| | | | | 606/153 |
| 5,628,786 | A * | 5/1997 | Banas | B32B 27/08 |
| | | | | 623/1.13 |
| 5,628,792 | A * | 5/1997 | Lentell | A61F 2/2403 |
| | | | | 623/2.12 |
| 5,639,274 | A * | 6/1997 | Fischell | A61F 2/958 |
| | | | | 606/108 |
| 5,665,115 | A * | 9/1997 | Cragg | A61F 2/966 |
| | | | | 623/1.13 |
| 5,716,417 | A * | 2/1998 | Girard | A61F 2/2418 |
| | | | | 623/2.38 |
| 5,728,068 | A * | 3/1998 | Leone | A61M 25/1011 |
| | | | | 623/1.11 |
| 5,749,890 | A * | 5/1998 | Shaknovich | A61F 2/958 |
| | | | | 606/198 |
| 5,756,476 | A * | 5/1998 | Epstein | C12N 15/113 |
| | | | | 435/375 |
| 5,769,812 | A * | 6/1998 | Stevens | A61M 25/0662 |
| | | | | 604/509 |
| 5,800,508 | A * | 9/1998 | Goicoechea | A61F 2/07 |
| | | | | 623/1.15 |
| 5,840,081 | A * | 11/1998 | Andersen | A61F 2/2475 |
| | | | | 606/108 |
| 5,843,161 | A * | 12/1998 | Solovay | A61F 2/958 |
| | | | | 623/1.13 |
| 5,855,597 | A * | 1/1999 | Jayaraman | A61F 2/2412 |
| | | | | 623/1.16 |
| 5,855,601 | A * | 1/1999 | Bessler | A61F 2/2418 |
| | | | | 623/2.38 |
| 5,855,602 | A * | 1/1999 | Angell | A61F 2/2427 |
| | | | | 606/1 |
| 5,925,063 | A | 7/1999 | Khosravi | |
| 5,957,949 | A | 9/1999 | Leonhardt et al. | |
| 6,027,525 | A | 2/2000 | Suh et al. | |
| 6,110,198 | A * | 8/2000 | Fogarty | A61F 2/915 |
| | | | | 623/1.36 |
| 6,132,473 | A * | 10/2000 | Williams | A61F 2/2415 |
| | | | | 623/66.1 |
| 6,168,614 | B1 * | 1/2001 | Andersen | A61F 2/2433 |
| | | | | 623/2.15 |
| 6,171,335 | B1 * | 1/2001 | Wheatley | A61F 2/2412 |
| | | | | 623/2.12 |
| 6,174,327 | B1 * | 1/2001 | Mertens | A61F 2/958 |
| | | | | 606/108 |
| 6,210,408 | B1 * | 4/2001 | Chandrasekaran | A61M 25/10 |
| | | | | 606/41 |
| 6,217,585 | B1 | 4/2001 | Houser et al. | |
| 6,221,091 | B1 * | 4/2001 | Khosravi | A61B 17/12109 |
| | | | | 623/1.24 |
| 6,231,602 | B1 * | 5/2001 | Carpentier | A61F 2/2445 |
| | | | | 623/2.36 |
| 6,245,102 | B1 | 6/2001 | Jayaraman | |
| 6,299,637 | B1 | 10/2001 | Shaolian et al. | |
| 6,302,906 | B1 * | 10/2001 | Goicoechea | A61F 2/82 |
| | | | | 623/1.11 |
| 6,350,277 | B1 | 2/2002 | Kocur | |
| 6,352,547 | B1 * | 3/2002 | Brown | B25B 27/146 |
| | | | | 606/1 |
| 6,352,554 | B2 * | 3/2002 | De Paulis | A61F 2/06 |
| | | | | 623/1.29 |
| 6,440,764 | B1 | 8/2002 | Focht et al. | |
| 6,454,799 | B1 * | 9/2002 | Schreck | A61F 2/2433 |
| | | | | 623/2.14 |
| 6,461,382 | B1 * | 10/2002 | Cao | A61F 2/2409 |
| | | | | 623/2.19 |
| 6,468,660 | B2 | 10/2002 | Ogle et al. | |
| 6,482,228 | B1 | 11/2002 | Norred | |
| 6,488,704 | B1 * | 12/2002 | Connelly | A61B 5/0002 |
| | | | | 623/1.15 |
| 6,527,979 | B2 | 3/2003 | Constantz et al. | |
| 6,605,112 | B1 * | 8/2003 | Moll | A61F 2/2475 |
| | | | | 623/1.24 |
| 6,614,115 | B2 * | 9/2003 | Focht | H01L 21/0262 |
| | | | | 257/745 |
| 6,689,123 | B2 * | 2/2004 | Pinchasik | A61F 2/958 |
| | | | | 606/1 |
| 6,716,244 | B2 * | 4/2004 | Klaco | A61F 2/2409 |
| | | | | 623/2.4 |
| 6,729,356 | B1 * | 5/2004 | Baker | D03D 3/08 |
| | | | | 28/142 |
| 6,733,525 | B2 * | 5/2004 | Yang | A61F 2/2427 |
| | | | | 623/2.14 |
| 6,769,161 | B2 * | 8/2004 | Brown | A61F 2/9524 |
| | | | | 72/402 |
| 6,783,542 | B2 | 8/2004 | Eidenschink | |
| 6,830,584 | B1 * | 12/2004 | Seguin | A61F 2/2436 |
| | | | | 623/2.11 |
| 6,878,162 | B2 * | 4/2005 | Bales | A61F 2/88 |
| | | | | 623/1.22 |
| 6,908,481 | B2 * | 6/2005 | Cribier | A61F 2/2418 |
| | | | | 623/2.11 |
| 6,911,040 | B2 * | 6/2005 | Johnson | A61F 2/07 |
| | | | | 623/1.13 |
| 7,018,406 | B2 * | 3/2006 | Seguin | A61F 2/2436 |
| | | | | 623/2.1 |
| 7,096,554 | B2 * | 8/2006 | Austin | A61F 2/9524 |
| | | | | 72/286 |
| 7,225,518 | B2 * | 6/2007 | Eidenschink | B25B 27/10 |
| | | | | 29/515 |
| 7,264,632 | B2 * | 9/2007 | Wright | A61F 2/95 |
| | | | | 623/1.11 |
| 7,276,078 | B2 * | 10/2007 | Spenser | A61F 2/2418 |
| | | | | 623/1.24 |
| 7,276,084 | B2 * | 10/2007 | Yang | A61F 2/2412 |
| | | | | 623/2.14 |
| 7,318,278 | B2 * | 1/2008 | Zhang | A61F 2/2418 |
| | | | | 29/458 |
| 7,374,571 | B2 | 5/2008 | Pease et al. | |
| 7,393,360 | B2 * | 7/2008 | Spenser | A61F 2/2412 |
| | | | | 623/2.18 |
| 7,415,861 | B2 * | 8/2008 | Sokel | A61F 2/9524 |
| | | | | 72/402 |
| 7,462,191 | B2 | 12/2008 | Spenser et al. | |
| 7,470,284 | B2 * | 12/2008 | Lambrecht | A61F 2/2418 |
| | | | | 623/2.11 |
| 7,563,280 | B2 * | 7/2009 | Anderson | A61F 2/2412 |
| | | | | 623/2.13 |
| 7,618,447 | B2 * | 11/2009 | Case | A61F 2/2475 |
| | | | | 623/2.14 |
| 7,785,341 | B2 * | 8/2010 | Forster | A61F 2/2433 |
| | | | | 606/194 |
| 7,785,366 | B2 * | 8/2010 | Maurer | A61F 2/246 |
| | | | | 623/2.1 |
| 7,959,672 | B2 * | 6/2011 | Salahieh | A61F 2/2412 |
| | | | | 623/2.14 |
| 8,029,556 | B2 * | 10/2011 | Rowe | A61F 2/2481 |
| | | | | 623/1.21 |
| 8,038,707 | B2 * | 10/2011 | Bales | A61F 2/915 |
| | | | | 623/1.22 |
| 8,052,749 | B2 * | 11/2011 | Salahieh | A61F 2/2439 |
| | | | | 623/2.12 |
| 8,182,530 | B2 * | 5/2012 | Huber | A61F 2/90 |
| | | | | 623/2.11 |
| 8,449,606 | B2 * | 5/2013 | Eliasen | A61F 2/246 |
| | | | | 623/2.11 |
| 8,500,683 | B2 * | 8/2013 | Constantz | A61M 29/02 |
| | | | | 604/96.01 |
| 8,512,391 | B2 * | 8/2013 | Bales, Jr. | A61F 2/915 |
| | | | | 623/1.22 |
| 8,652,203 | B2 * | 2/2014 | Quadri | A61F 2/2436 |
| | | | | 623/2.11 |

(56) References Cited

U.S. PATENT DOCUMENTS

| | | | | |
|---|---|---|---|---|
| 8,747,463 B2* | 6/2014 | Fogarty | A61F 2/2409 | 623/2.38 |
| 8,992,608 B2* | 3/2015 | Haug | A61F 2/2436 | 623/2.38 |
| 9,232,999 B2* | 1/2016 | Maurer | A61F 2/246 | |
| 9,393,110 B2* | 7/2016 | Levi | A61F 2/2433 | |
| 9,554,927 B2* | 1/2017 | Bales | A61F 2/88 | |
| 10,433,958 B2* | 10/2019 | Levi | A61F 2/2418 | |
| 10,433,959 B2* | 10/2019 | Levi | A61F 2/2418 | |
| 10,463,509 B2* | 11/2019 | Bales, Jr. | A61F 2/915 | |
| 10,478,292 B2* | 11/2019 | Levi | A61F 2/2433 | |
| 10,478,294 B2* | 11/2019 | Taylor | A61F 2/2433 | |
| 10,729,543 B2* | 8/2020 | Levi | A61F 2/2418 | |
| 10,849,743 B2* | 12/2020 | Levi | A61F 2/2433 | |
| 11,096,781 B2* | 8/2021 | Gurovich | A61F 2/2418 | |
| 11,135,056 B2* | 10/2021 | Gurovich | A61F 2/2418 | |
| 11,224,509 B2* | 1/2022 | Dasi | A61L 27/16 | |
| 11,628,062 B2* | 4/2023 | Levi | A61F 2/2412 | 623/2.14 |
| 11,744,704 B2* | 9/2023 | Taylor | A61F 2/2433 | 623/2.11 |
| 11,793,632 B2* | 10/2023 | Levi | A61F 2/2418 | |
| 2001/0021872 A1* | 9/2001 | Bailey | A61F 2/07 | 623/1.26 |
| 2002/0026094 A1* | 2/2002 | Roth | A61B 17/00234 | 600/203 |
| 2002/0032481 A1 | 3/2002 | Gabbay | | |
| 2002/0138135 A1* | 9/2002 | Duerig | A61F 2/2475 | 623/1.24 |
| 2002/0173842 A1 | 11/2002 | Buchanan | | |
| 2003/0050694 A1 | 3/2003 | Yang et al. | | |
| 2003/0100939 A1 | 5/2003 | Yodfat et al. | | |
| 2003/0114913 A1* | 6/2003 | Spenser | A61F 2/243 | 623/2.14 |
| 2003/0158597 A1* | 8/2003 | Quiachon | A61F 2/958 | 623/1.23 |
| 2003/0199820 A1* | 10/2003 | Constantz | A61M 29/02 | 604/101.04 |
| 2003/0212454 A1* | 11/2003 | Scott | A61F 2/2412 | 623/2.14 |
| 2004/0186563 A1* | 9/2004 | Lobbi | A61F 2/2418 | 623/2.11 |
| 2004/0260389 A1* | 12/2004 | Case | A61F 2/2475 | 623/2.38 |
| 2005/0010285 A1 | 1/2005 | Lambrecht et al. | | |
| 2005/0033404 A1* | 2/2005 | Eidenschink | A61F 2/958 | 623/1.11 |
| 2005/0075725 A1* | 4/2005 | Rowe | A61F 2/2418 | 623/2.14 |
| 2005/0075728 A1* | 4/2005 | Nguyen | A61F 2/2418 | 623/1.26 |
| 2005/0159807 A1* | 7/2005 | Bales | A61F 2/88 | 623/1.15 |
| 2005/0188525 A1* | 9/2005 | Weber | B25B 27/10 | 29/508 |
| 2005/0203614 A1 | 9/2005 | Forster et al. | | |
| 2005/0234546 A1* | 10/2005 | Nugent | A61F 2/2433 | 623/2.11 |
| 2006/0004469 A1 | 1/2006 | Sokel | | |
| 2006/0025857 A1* | 2/2006 | Bergheim | A61L 27/50 | 623/2.18 |
| 2006/0058872 A1 | 3/2006 | Salahieh et al. | | |
| 2006/0074484 A1 | 4/2006 | Huber | | |
| 2006/0149350 A1* | 7/2006 | Patel | A61F 2/014 | 623/1.11 |
| 2006/0178740 A1* | 8/2006 | Stacchino | A61F 2/2436 | 623/2.18 |
| 2006/0183383 A1* | 8/2006 | Asmus | B25B 27/10 | 439/843 |
| 2006/0229719 A1* | 10/2006 | Marquez | A61F 2/2418 | 623/2.18 |
| 2006/0259136 A1* | 11/2006 | Nguyen | A61F 2/2412 | 623/2.18 |
| 2006/0259137 A1 | 11/2006 | Artof et al. | | |
| 2006/0287717 A1* | 12/2006 | Rowe | A61F 2/2445 | 623/2.11 |
| 2007/0010876 A1* | 1/2007 | Salahieh | A61F 2/2418 | 623/2.11 |
| 2007/0010877 A1* | 1/2007 | Salahieh | A61F 2/2409 | 623/2.11 |
| 2007/0112422 A1* | 5/2007 | Dehdashtian | A61F 2/2427 | 623/2.11 |
| 2007/0162102 A1* | 7/2007 | Ryan | A61F 2/958 | 623/1.12 |
| 2007/0203503 A1* | 8/2007 | Salahieh | A61F 2/2436 | 623/2.11 |
| 2007/0203575 A1* | 8/2007 | Forster | A61F 2/2439 | 623/2.11 |
| 2007/0203576 A1* | 8/2007 | Lee | A61F 2/2412 | 623/2.14 |
| 2007/0213813 A1* | 9/2007 | Von Segesser | A61F 2/2433 | 623/2.11 |
| 2007/0233228 A1* | 10/2007 | Eberhardt | H01M 4/131 | 623/1.13 |
| 2007/0260305 A1* | 11/2007 | Drews | A61F 2/243 | 623/2.11 |
| 2007/0265700 A1* | 11/2007 | Eliasen | A61F 2/246 | 623/2.1 |
| 2008/0114442 A1* | 5/2008 | Mitchell | A61F 2/95 | 623/1.13 |
| 2008/0154355 A1 | 6/2008 | Benichou et al. | | |
| 2008/0183271 A1* | 7/2008 | Frawley | A61F 2/958 | 623/1.11 |
| 2008/0243245 A1* | 10/2008 | Thambar | A61F 2/2436 | 623/2.11 |
| 2008/0275537 A1* | 11/2008 | Limon | A61F 2/915 | 264/239 |
| 2009/0125118 A1* | 5/2009 | Gong | A61F 2/0077 | 623/23.7 |
| 2009/0157175 A1* | 6/2009 | Benichou | A61F 2/2418 | 623/2.18 |
| 2009/0264986 A1* | 10/2009 | Bales | A61F 2/915 | 623/1.22 |
| 2009/0276040 A1* | 11/2009 | Rowe | A61F 2/90 | 623/2.18 |
| 2009/0281619 A1* | 11/2009 | Le | A61M 25/01 | 623/2.11 |
| 2009/0299452 A1* | 12/2009 | Eidenschink | A61F 2/9526 | 623/1.11 |
| 2009/0319037 A1* | 12/2009 | Rowe | A61F 2/2427 | 623/2.11 |
| 2010/0004735 A1* | 1/2010 | Yang | A61F 2/91 | 623/1.34 |
| 2010/0049313 A1* | 2/2010 | Alon | A61F 2/2418 | 623/2.11 |
| 2010/0082094 A1* | 4/2010 | Quadri | A61F 2/2412 | 29/890.132 |
| 2010/0168844 A1* | 7/2010 | Toomes | A61F 2/2418 | 623/2.18 |
| 2010/0185277 A1* | 7/2010 | Braido | A61F 2/2409 | 623/2.37 |
| 2010/0204781 A1* | 8/2010 | Alkhatib | A61F 2/2418 | 623/1.26 |
| 2011/0015729 A1* | 1/2011 | Jimenez | A61F 2/2427 | 623/2.11 |
| 2011/0137397 A1* | 6/2011 | Chau | A61F 2/24 | 623/2.37 |
| 2011/0218619 A1* | 9/2011 | Benichou | A61F 2/2418 | 623/2.11 |
| 2011/0276129 A1* | 11/2011 | Salahieh | A61F 2/2439 | 623/2.18 |
| 2012/0029628 A1* | 2/2012 | Rowe | A61F 2/2445 | 623/2.11 |
| 2012/0030090 A1* | 2/2012 | Johnston | G06Q 40/00 | 705/37 |
| 2012/0071969 A1* | 3/2012 | Li | A61F 2/2418 | 623/2.17 |
| 2012/0089223 A1* | 4/2012 | Nguyen | A61F 2/2418 | 623/2.14 |

(56)　　　　　References Cited

U.S. PATENT DOCUMENTS

| | | | | |
|---|---|---|---|---|
| 2012/0101571 A1* | 4/2012 | Thambar | A61B 17/0057 | |
| | | | 623/2.17 | |
| 2012/0123529 A1* | 5/2012 | Levi | A61F 2/2418 | |
| | | | 623/2.11 | |
| 2012/0185038 A1* | 7/2012 | Fish | A61F 2/2418 | |
| | | | 493/405 | |
| 2012/0259409 A1* | 10/2012 | Nguyen | A61F 2/2415 | |
| | | | 623/2.15 | |
| 2013/0023985 A1* | 1/2013 | Khairkhahan | A61F 2/2463 | |
| | | | 623/2.38 | |
| 2013/0046373 A1* | 2/2013 | Cartledge | A61F 2/966 | |
| | | | 623/1.11 | |
| 2013/0150956 A1* | 6/2013 | Yohanan | A61F 2/2433 | |
| | | | 623/2.14 | |
| 2013/0166017 A1* | 6/2013 | Cartledge | A61F 2/2439 | |
| | | | 623/1.2 | |
| 2013/0190857 A1* | 7/2013 | Mitra | A61L 31/06 | |
| | | | 623/1.36 | |
| 2013/0274873 A1* | 10/2013 | Delaloye | A61F 2/2409 | |
| | | | 623/2.18 | |
| 2013/0331929 A1* | 12/2013 | Mitra | A61F 2/2418 | |
| | | | 623/2.11 | |
| 2013/0338759 A1* | 12/2013 | Bales, Jr. | A61F 2/88 | |
| | | | 623/1.22 | |
| 2014/0121766 A1* | 5/2014 | Salahieh | A61F 2/2418 | |
| | | | 623/2.12 | |
| 2014/0194981 A1* | 7/2014 | Menk | A61F 2/2418 | |
| | | | 623/2.17 | |
| 2014/0200661 A1* | 7/2014 | Pintor | A61F 2/2409 | |
| | | | 623/2.18 | |
| 2014/0209238 A1* | 7/2014 | Bonyuet | A61F 2/2415 | |
| | | | 156/294 | |
| 2014/0222136 A1* | 8/2014 | Geist | A61F 2/2436 | |
| | | | 623/2.37 | |
| 2014/0277417 A1* | 9/2014 | Schraut | A61F 2/2418 | |
| | | | 623/2.17 | |
| 2014/0277419 A1* | 9/2014 | Garde | A61F 2/2403 | |
| | | | 623/2.18 | |
| 2014/0277424 A1* | 9/2014 | Oslund | A61F 2/2436 | |
| | | | 623/2.38 | |
| 2014/0277563 A1* | 9/2014 | White | A61F 2/243 | |
| | | | 623/23.7 | |
| 2014/0330372 A1* | 11/2014 | Weston | A61F 2/2418 | |
| | | | 623/2.37 | |
| 2014/0343671 A1* | 11/2014 | Yohanan | A61F 2/2418 | |
| | | | 623/2.18 | |
| 2014/0350667 A1* | 11/2014 | Braido | A61F 2/2409 | |
| | | | 623/2.11 | |
| 2015/0073545 A1* | 3/2015 | Braido | A61F 2/2412 | |
| | | | 623/2.18 | |
| 2016/0374802 A1* | 12/2016 | Levi | A61F 2/2433 | |
| | | | 623/2.14 | |
| 2018/0028310 A1* | 2/2018 | Gurovich | A61F 2/2433 | |
| 2018/0325665 A1 | 11/2018 | Gurovich et al. | | |
| 2019/0159894 A1* | 5/2019 | Levi | A61F 2/2418 | |
| 2019/0192288 A1* | 6/2019 | Levi | A61F 2/2433 | |
| 2019/0192289 A1* | 6/2019 | Levi | A61F 2/2433 | |
| 2020/0100895 A1* | 4/2020 | Levi | A61F 2/2418 | |

FOREIGN PATENT DOCUMENTS

| | | | | |
|---|---|---|---|---|
| DE | 144167 C | 9/1903 | | |
| DE | 2246526 A1 * | 3/1973 | | |
| DE | 19532846 A1 * | 3/1997 | A61F 2/2418 | |
| DE | 19546692 A1 * | 6/1997 | A61F 2/2418 | |
| DE | 19857887 A1 * | 7/2000 | A61F 2/2418 | |
| DE | 19907646 A1 * | 8/2000 | A61F 2/2433 | |
| DE | 10049812 A1 * | 4/2002 | A61F 2/012 | |
| DE | 10049813 C1 * | 4/2002 | A61B 17/320783 | |
| DE | 10049814 A1 * | 4/2002 | A61F 2/92 | |
| DE | 10049815 A1 * | 4/2002 | A61B 17/320758 | |
| EP | 0103546 A1 * | 3/1984 | A61F 2/2427 | |
| EP | 0850607 A1 | 7/1998 | | |
| EP | 1057460 A1 * | 12/2000 | A61F 2/2418 | |
| EP | 1088529 A2 * | 4/2001 | A61F 2/2448 | |
| EP | 1570809 A1 * | 9/2005 | A61F 2/2418 | |
| FR | 2788217 A1 * | 7/2000 | A61F 2/2412 | |
| FR | 2815844 A1 * | 5/2002 | A61F 2/2418 | |
| SU | 1271508 A1 | 11/1986 | | |
| WO | WO-9117720 A * | 11/1991 | | |
| WO | WO-1991017720 A1 | 11/1991 | | |
| WO | WO-9217118 A1 * | 10/1992 | A61B 17/320725 | |
| WO | WO-1992017118 A1 | 10/1992 | | |
| WO | WO-9301768 A1 * | 2/1993 | A61F 2/2436 | |
| WO | WO-1993001768 A1 | 2/1993 | | |
| WO | WO-1997024080 A1 | 7/1997 | | |
| WO | WO-1999030646 A1 | 6/1999 | | |
| WO | WO-9933414 A1 * | 7/1999 | A61F 2/243 | |
| WO | WO-1999033414 A1 | 7/1999 | | |
| WO | WO-9940964 A1 * | 8/1999 | A61M 25/104 | |
| WO | WO-1999040964 A1 | 8/1999 | | |
| WO | WO-9947075 A1 * | 9/1999 | A61F 2/95 | |
| WO | WO-1999047075 A1 | 9/1999 | | |
| WO | WO-0018333 A1 * | 4/2000 | A61F 2/2409 | |
| WO | WO-2000018333 A1 | 4/2000 | | |
| WO | WO-0041652 A1 * | 7/2000 | A61F 2/2418 | |
| WO | WO-2000041652 A1 | 7/2000 | | |
| WO | WO-0047139 A1 * | 8/2000 | A61F 2/2418 | |
| WO | WO-2000047139 A1 | 8/2000 | | |
| WO | WO-0135878 A2 * | 5/2001 | A61F 7/02 | |
| WO | WO-2001035878 A2 | 5/2001 | | |
| WO | WO-0149213 A2 * | 7/2001 | A61F 2/2475 | |
| WO | WO-2001049213 A2 | 7/2001 | | |
| WO | WO-0154624 A1 * | 8/2001 | A61F 2/2412 | |
| WO | WO-0154625 A1 * | 8/2001 | A61F 2/2475 | |
| WO | WO-0162189 A1 * | 8/2001 | A61F 2/2418 | |
| WO | WO-2001054624 A1 | 8/2001 | | |
| WO | WO-2001054625 A1 | 8/2001 | | |
| WO | WO-2001062189 A1 | 8/2001 | | |
| WO | WO-0164137 A1 * | 9/2001 | A61F 2/2418 | |
| WO | WO-2001064137 A1 | 9/2001 | | |
| WO | WO-0176510 A2 * | 10/2001 | A61F 2/2436 | |
| WO | WO-2001076510 A2 | 10/2001 | | |
| WO | WO-2002022054 A1 | 3/2002 | | |
| WO | WO-0241789 A2 * | 5/2002 | A61B 17/0487 | |
| WO | WO-2002036048 A1 | 5/2002 | | |
| WO | WO-2002041789 A2 | 5/2002 | | |
| WO | WO-0243620 A1 * | 6/2002 | A61F 2/2418 | |
| WO | WO-0247575 A2 * | 6/2002 | A61F 2/2418 | |
| WO | WO-0249540 A2 * | 6/2002 | A61F 2/2409 | |
| WO | WO-2002043620 A1 | 6/2002 | | |
| WO | WO-2002047575 A2 | 6/2002 | | |
| WO | WO-2002049540 A2 | 6/2002 | | |
| WO | WO-03047468 A1 * | 6/2003 | A61F 2/2427 | |
| WO | WO-2003047468 A1 | 6/2003 | | |
| WO | WO-2005055883 A1 * | 6/2005 | A61F 2/2445 | |
| WO | WO-2005102015 A2 * | 11/2005 | A61F 2/2409 | |
| WO | WO-2006014233 A2 * | 2/2006 | A61F 2/91 | |
| WO | WO-2006032051 A2 * | 3/2006 | A61B 17/00234 | |
| WO | WO-2006034008 A2 * | 3/2006 | A61F 2/95 | |
| SU | WO-2006111391 A1 * | 10/2006 | A61F 2/2427 | |
| WO | WO-2006127089 A1 * | 11/2006 | A61F 2/82 | |
| WO | WO-2006138173 A2 * | 12/2006 | A61F 2/2433 | |
| WO | WO-2007047488 A2 * | 4/2007 | A61F 2/9517 | |
| WO | WO-2007067942 A1 * | 6/2007 | A61F 2/2409 | |
| WO | WO-2008005405 A2 * | 1/2008 | A61M 25/1002 | |
| WO | WO-2008015257 A2 * | 2/2008 | A61F 2/844 | |
| WO | WO-2008035337 A2 * | 3/2008 | A61F 2/2436 | |
| WO | WO-2008091515 A2 * | 7/2008 | A61F 2/82 | |
| WO | WO-2008147964 A1 * | 12/2008 | A61F 2/2418 | |
| WO | WO-2008150529 A1 * | 12/2008 | A61F 2/2418 | |
| WO | WO-2009033469 A1 * | 3/2009 | A61F 2/2487 | |
| WO | WO-2009042196 A2 * | 4/2009 | A61F 2/2412 | |
| WO | WO-2009053497 A1 * | 4/2009 | A61F 2/2436 | |
| WO | WO-2009061389 A2 * | 5/2009 | A61F 2/2418 | |
| WO | WO-2009094188 A2 * | 7/2009 | A61F 2/2418 | |
| WO | WO-2009116041 A2 * | 9/2009 | A61F 2/2418 | |
| WO | WO-2009149462 A2 * | 12/2009 | E03C 1/025 | |
| WO | WO-2010011699 A2 * | 1/2010 | A61F 2/2418 | |
| WO | WO-2010121076 A2 * | 10/2010 | A61F 2/9522 | |
| WO | WO-2013106585 A1 * | 7/2013 | A61F 2/2418 | |

(56) References Cited

FOREIGN PATENT DOCUMENTS

| | | | | |
|---|---|---|---|---|
| WO | WO-2015085218 A1 * | 6/2015 | ............. | B29C 49/26 |
| WO | WO-2022103926 A1 * | 5/2022 | ........... | A61F 2/2415 |
| WO | WO-2022159427 A1 * | 7/2022 | ........... | A61F 2/2433 |

OTHER PUBLICATIONS

Bailey S.R., "Percutaneous Expandable Prosthetic Valves," Text-book of Interventional Cardiology, 1994, vol. 2, 2nd Edition, pp. 1268-1276 (12 Pages).

Pavcnik D., et al., "Development and Initial Experimental Evalua-tion of a Prosthetic Aortic Valve for Transcatheter Placement," Cardiovascular Radiology, Apr. 1, 1992, vol. 183(1), pp. 151-154.

Ross, "Aortic Valve Surgery," Surgery of the Arotic Valves, Guy's Hospital, London, At a meeting of the Council on Aug. 4, 1966. pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Walther T., etal, "Trans-catheter Valve-in-valve Implantation: In Vitro Hydrodynamic Performance of the SAPIEN + Cloth Trans-Catheter Heart Valve in the Carpentier-Edwards Perimount Valves," European Journal of Cardio-Thoracic Surgery, 2011, vol. 40, p. 1 120- 1126, (Sep. 23, 2010).

Wheatley D. J., "Valve Prostheses," Operative Surgery, 4th edition, 1986, pp. 415-424.

* cited by examiner

PROSTHETIC HEART VALVE LEAFLET ASSEMBLIES AND METHODS

CROSS-REFERENCE TO RELATED APPLICATIONS

This application is a divisional of U.S. application Ser. No. 18/195,288, filed May 9, 2023, which is a continuation of International Application No. PCT/US2021/058918, filed Nov. 11, 2021, which claims the benefit of U.S. Provisional Application No. 63/113,034, filed Nov. 12, 2020, each of which are incorporated herein by reference in their entirety.

FIELD

The present disclosure relates to prosthetic heart valves, and to methods and assemblies for forming leaflet assemblies and attached leaflet assemblies to a frame of a prosthetic heart valve.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size. Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Most expandable, transcatheter heart valves comprise a cylindrical metal frame or stent and prosthetic leaflets mounted inside the frame. Typically, the leaflets are secured to a circumferential skirt, attached to an inner surface of the frame of the prosthetic valve. Such a traditional skirt can serve as an attachment surface for the valve leaflets, while also establishing a seal with the native tissue when the prosthetic valve is placed at the implantation site. However, since the skirt can span an entire circumference of the inner surface of the frame, attachment of multiple leaflets (e.g., three leaflets) to the skirt may be time consuming and require delicate assembly skills to ensure proper attachment.

Accordingly, a need exists for improved prosthetic heart valve leaflet assemblies and methods for assembling the leaflet assemblies to a frame of the prosthetic heart valve.

SUMMARY

Described herein are examples of prosthetic heart valves, leaflet assemblies for prosthetic heart valves, leaflet sub-assemblies of a leaflet assembly, and methods for assembling leaflet sub-assemblies, leaflet assemblies including a plurality of leaflet sub-assemblies, and prosthetic heart valves including the leaflet assemblies. The prosthetic heart valves may include a frame and a leaflet assembly attached to the frame. The leaflet assembly can include a plurality of leaflets, adjacent leaflets of which are coupled to one another at commissures. Such commissures can be reinforced in such a manner that the amount of fabric material at the commissure is minimized. As a result, the leaflet assembly may be more easily assembled off the frame of the prosthetic heart valve, while retaining the strength and stiffness of the commissure and reducing the amount of fabric therein.

In a representative example, a method of assembling a valvular structure can comprise folding an integral upper tab of a first leaflet onto an integral lower tab of the first leaflet such that a first surface of the upper tab contacts a first surface of the lower tab, and disposing a first end portion of a reinforcing member on a second surface of the upper tab of the first leaflet, and coupling the first end portion of the reinforcing member, the upper and lower tabs of the first leaflet, and the commissure member to one another using one or more fastening sutures. The method can further comprise folding an integral upper tab of a second leaflet onto an integral lower tab of the second leaflet such that a first surface of the upper tab contacts a first surface of the lower tab, disposing the second leaflet adjacent the first leaflet such that the commissure member is positioned between the respective lower tabs, disposing a second end portion of the reinforcing member on a second surface of the upper tab of the second leaflet, and coupling the second end portion of the reinforcing member, the upper and lower tabs of the second leaflet, and the commissure member to one another using the one or more fastening sutures to form a commissure.

In another representative example, a method of assembling a prosthetic heart valve including a valvular structure can comprise disposing a first end portion of a reinforcing member an upper tab of a first leaflet, the upper tab disposed over a respective lower tab, disposing a commissure member adjacent the lower tab of the first leaflet, the commissure member folded to form first and second layers, and coupling the first end portion of the reinforcing member, the upper and lower tabs of the first leaflet, and the commissure member to one another using one or more fastening sutures. The method can further comprise disposing a second leaflet adjacent the first leaflet such that the first and second layers of the commissure member are positioned between a lower tab of the second leaflet and the lower tab of the first leaflet, disposing a second end portion of the reinforcing member on an upper tab of the second leaflet, and coupling the second end portion of the reinforcing member, the upper and lower tabs of the second leaflet, and the commissure member to one another using the one or more fastening sutures to form a commissure. The method can further comprise cutting first and second lateral portions of the commissure member such that lateral edges of the commissure member do not extend past lateral edges of the upper and lower tabs of the first and second leaflets, sewing one or more securing sutures through the commissure such that they extend around lateral edges of the upper and lower tabs of the first and second leaflets to form a plurality of loops, sliding the plurality of loops axially over a commissure support portion of a frame of the prosthetic valve such that the leaflets are disposed within the frame, and tightening the plurality of loops to secure the leaflets to the frame.

In a representative example, a prosthetic heart valve can comprise a radially expandable and compressible annular frame comprising a plurality of expansion and locking mechanisms and a valvular structure comprising a plurality of commissures. Each commissure can comprise a first leaflet having an integral upper tab and an integral lower tab, the upper tab being folded over the lower tab, a second leaflet having an integral upper tab and an integral lower tab, the upper tab being folded over the lower tab, a commissure member disposed between the lower tabs of the first and second leaflets, and a reinforcing member having a first end portion disposed on the upper tab of the first leaflet and a second end portion disposed on the upper tab of the second leaflet. Each commissure can be coupled to a respective expansion and locking mechanism via a plurality of loops coupled to the commissure and extending around the expansion and locking mechanism, such that the valvular structure is disposed within and supported by the frame.

The foregoing and other objects, features, and advantages of the disclosure will become more apparent from the following detailed description, which proceeds with reference to the accompanying figures.

DETAILED DESCRIPTION

General Considerations

For purposes of this description, certain aspects, advantages, and novel features of the examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

Figure 1:
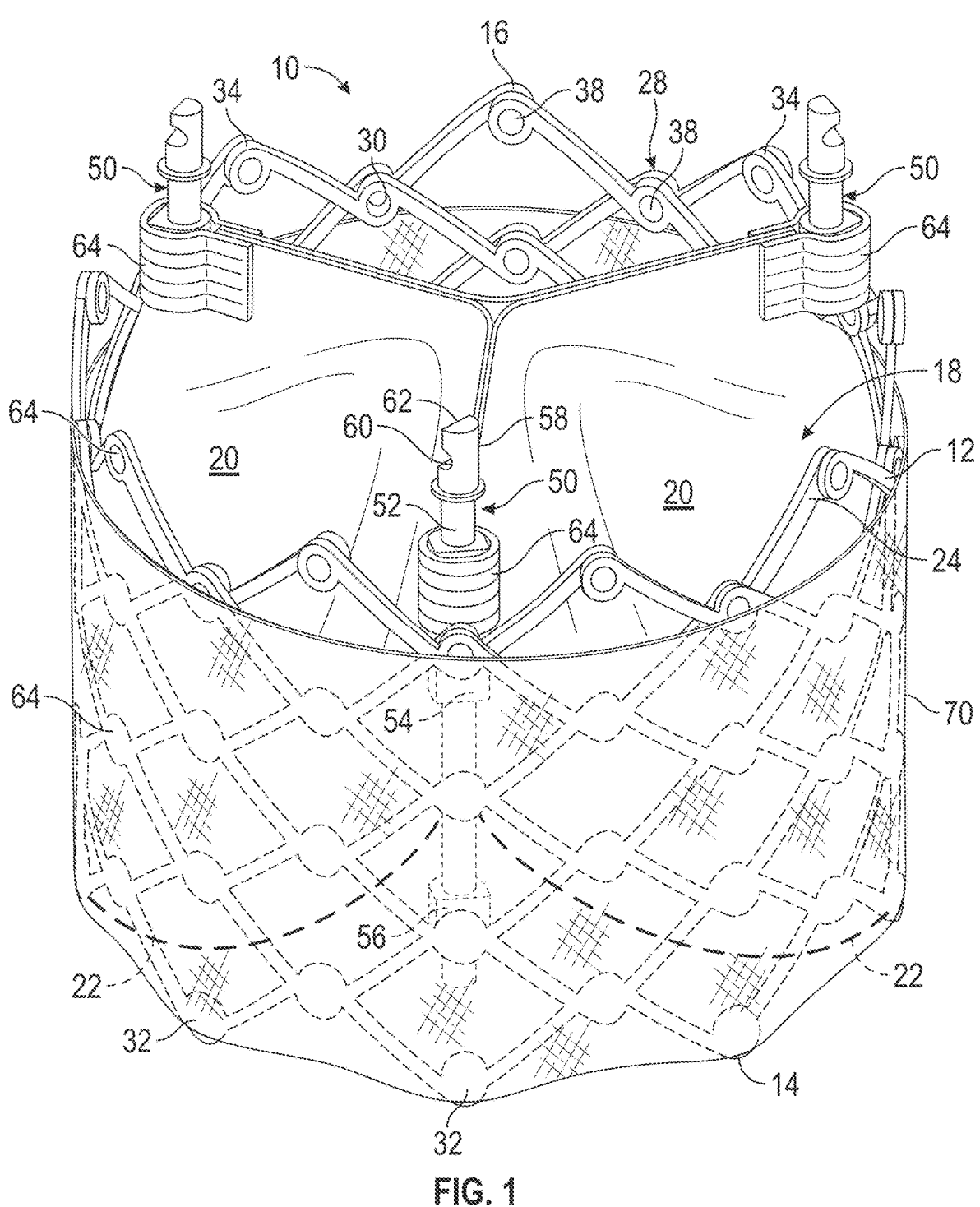
FIG. 1 is a perspective view of a prosthetic heart valve, according to one example.
Figure 2:
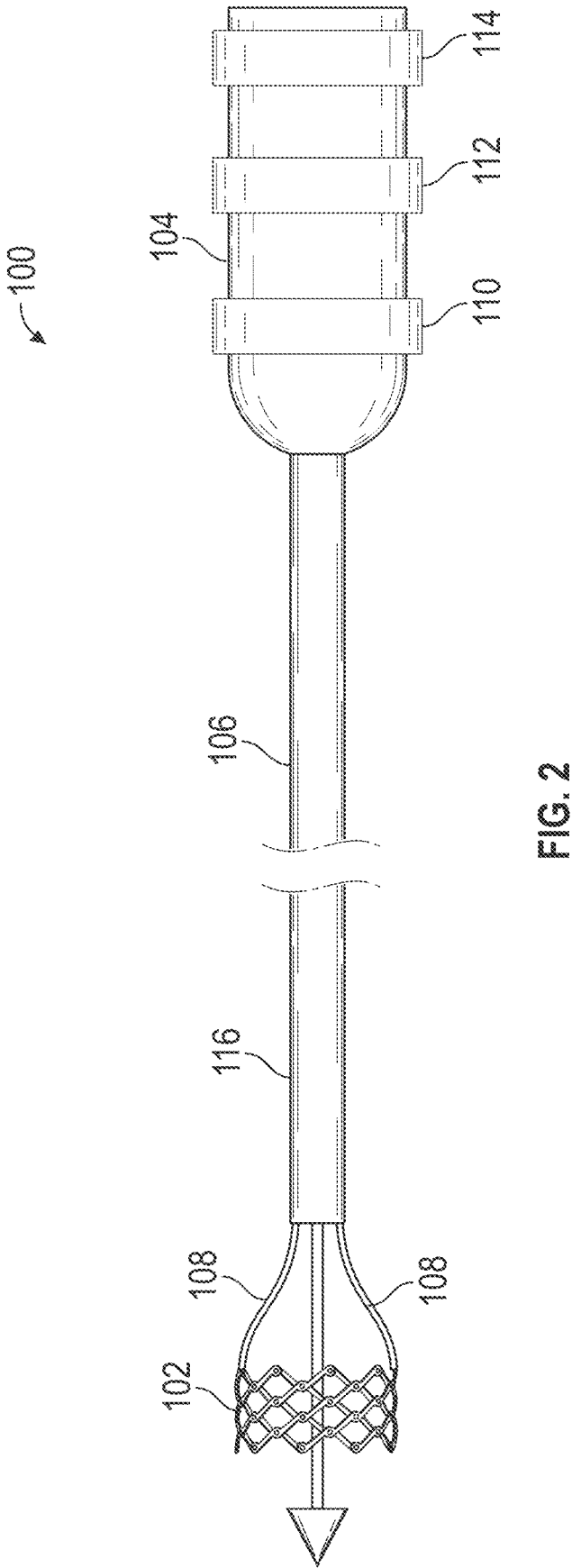
FIG. 2 is a side elevation view of a delivery apparatus for a prosthetic heart valve, according to one example.
Figure 3:
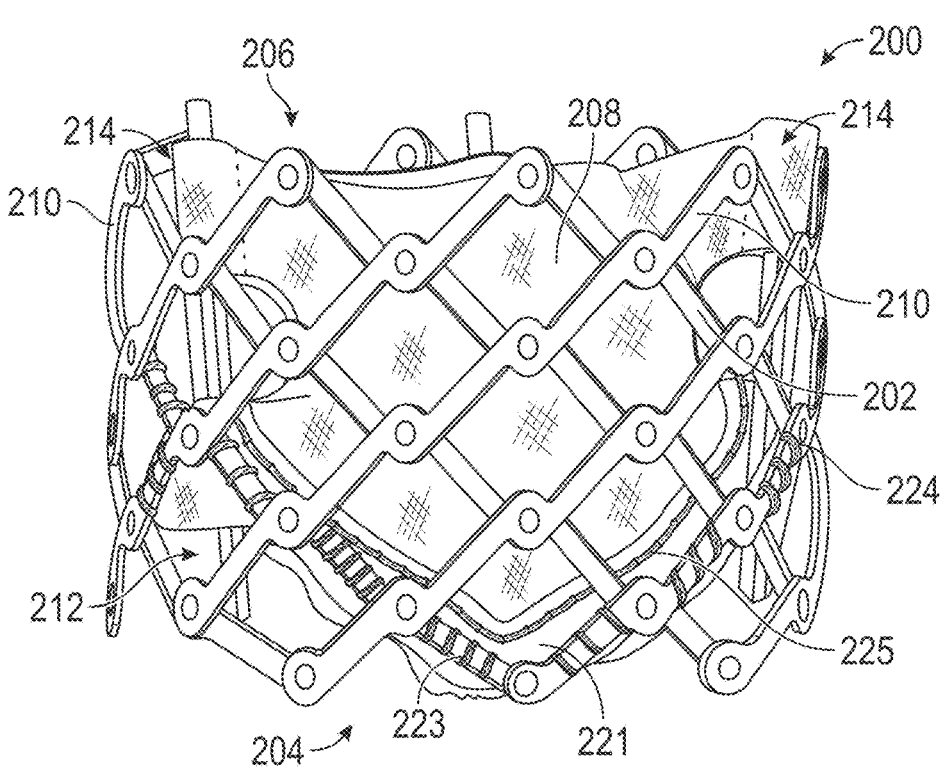
FIG. 3 is a perspective view of a prosthetic heart valve, according to one example.

All features described herein are independent of one another and, except where structurally impossible, can be used in combination with any other feature described herein. For example, a delivery apparatus 100 as shown in FIG. 2 can be used in combination with prosthetic valve 200 described herein. In another example, actuators 50 as shown in FIG. 1 can be used in combination with the prosthetic valve 200. In still other examples, commissure assemblies 214 as shown in FIG. 3 can be used with prosthetic valve 10.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

In view of the many possible examples to which the principles of the disclosure may be applied, it should be recognized that the illustrated examples are only preferred examples and should not be taken as limiting the scope. Rather, the scope is defined by the following claims. We therefore claim all that comes within the scope and spirit of these claims.

Examples of the Disclosed Technology

Described herein are examples of prosthetic heart valves, leaflet assemblies for prosthetic heart valves, leaflet sub-assemblies of a leaflet assembly, and methods for assembling leaflet sub-assemblies, leaflet assemblies including a plurality of leaflet sub-assemblies, and prosthetic heart valves including the leaflet assemblies. The prosthetic heart valves may include a frame and a leaflet assembly attached to the frame. The leaflet assembly can include a plurality of leaflets, adjacent leaflets of which are coupled to one another at commissures. Such commissures can be reinforced in such a manner that the amount of fabric material at the commissure is minimized. As a result, the leaflet assembly may be more easily assembled off the frame of the prosthetic heart valve, while retaining the strength and stiffness of the commissure and reducing the amount of fabric therein.

FIG. 1 shows an exemplary prosthetic valve 10, according to one example. The prosthetic valve 10 can include an annular stent or frame 12 having an inflow end 14 and an outflow end 16. The prosthetic valve 10 can also include a valvular structure 18 which is coupled to and supported inside of the frame 12. The valvular structure 18 is configured to regulate the flow of blood through the prosthetic valve 10 from the inflow end 14 to the outflow end 16.

The valvular structure 18 can include, for example, a leaflet assembly comprising one or more leaflets 20 made of a flexible material. The leaflets 20 can be made from in whole or part, biological material, bio-compatible synthetic materials, or other such materials. Suitable biological material can include, for example, bovine pericardium (or pericardium from other sources). The leaflets 20 can be secured to one another at their adjacent sides to form commissures, each of which can be secured to a respective actuator 50 or the frame 12.

In the depicted example, the valvular structure 18 comprises three leaflets 20, which can be arranged to collapse in a tricuspid arrangement. Each leaflet 20 can have an inflow edge portion 22. As shown in FIG. 1, the inflow edge portions 22 of the leaflets 20 can define an undulating, curved scallop shape that follows or tracks a plurality of interconnected strut segments of the frame 12 in a circumferential direction when the frame 12 is in the radially expanded configuration. The inflow edges of the leaflets can be referred to as a "scallop line."

In some examples, the inflow edge portions 22 of the leaflets 20 can be sutured to adjacent struts of the frame generally along the scallop line. In other examples, the inflow edge portions 22 of the leaflets 20 can be sutured to an inner skirt, which in turn in sutured to adjacent struts of the frame. By forming the leaflets 20 with this scallop geometry, stresses on the leaflets 20 are reduced, which in turn improves durability of the valve 10. Moreover, by virtue of the scallop shape, folds and ripples at the belly of each leaflet 20 (the central region of each leaflet), which can cause early calcification in those areas, can be eliminated or at least minimized. The scallop geometry also reduces the amount of tissue material used to form valvular structure 18, thereby allowing a smaller, more even crimped profile at the inflow end 14 of the valve 10.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, 8,252,202, 11,135,056, and 11,399, 932, all of which are incorporated herein by reference in their entireties.

The prosthetic valve 10 can be radially compressible and expandable between a radially compressed configuration and a radially expanded configuration. The frame 12 can include a plurality of interconnected lattice struts 24 arranged in a lattice-type pattern and forming a plurality of apices 34 at the outflow end 16 of the prosthetic valve 10. The struts 24 can also form similar apices 32 at the inflow end 14 of the prosthetic valve 10.

The struts 24 can be pivotably coupled to one another at one or more pivot joints or pivot junctions 28 along the length of each strut. For example, in one example, each of the struts 24 can be formed with apertures 30 at opposing ends of the strut and apertures spaced along the length of the strut. Respective hinges can be formed at the locations where struts 24 overlap each other via fasteners 38, such as rivets or pins that extend through the apertures 30. The hinges can allow the struts 24 to pivot relative to one another as the frame 12 is radially expanded or compressed, such as during assembly, preparation, or implantation of the prosthetic valve 10.

The frame struts and the components used to form the pivot joints of the frame 12 (or any frames described below) can be made of any of various suitable materials, such as stainless steel, a cobalt chromium alloy, or a nickel titanium alloy ("NiTi"), for example Nitinol. In some examples, the frame 12 can be constructed by forming individual components (e.g., the struts and fasteners of the frame) and then mechanically assembling and connecting the individual components together. Further details regarding the construction of the frame and the prosthetic valve are described in U.S. Pat. Nos. 10,603,165, 10,869,759, 10,806,573, and 11,446,141, all of which are incorporated herein by reference.

In the illustrated example, the prosthetic valve 10 can be mechanically expanded from the radially contracted configuration to the radially expanded configuration. For example, the prosthetic valve 10 can be radially expanded by maintaining the inflow end 14 of the frame 12 at a fixed position while applying a force in the axial direction against the outflow end 16 toward the inflow end 14. Alternatively, the prosthetic valve 10 can be expanded by applying an axial force against the inflow end 14 while maintaining the outflow end 16 at a fixed position, or by applying opposing axial forces to the inflow and outflow ends 14, 16, respectively.

As shown in FIG. 1, the prosthetic valve 10 can include one or more actuators 50 mounted to and equally spaced around the inner surface of the frame 12. Each of the actuators 50 can be configured to form a releasable connection with one or more respective actuators of a delivery apparatus.

In the illustrated example, expansion and compression forces can be applied to the frame by the actuators 50. Referring again to FIG. 1, each of the actuators 50 can comprise a screw or threaded rod 52, a first anchor in the form of a cylinder or sleeve 54, and a second anchor in the form of a threaded nut 56. The rod 52 extends through the sleeve 54 and the nut 56. The sleeve 54 can be secured to the frame 12, such as with a fastener 38 that forms a hinge at the junction between two struts. Each actuator 50 is configured to increase the distance between the attachment locations of a respective sleeve 54 and nut 56, which causes the frame 12 to elongate axially and compress radially, and to decrease the distance between the attachment locations of a respective sleeve 54 and nut 56, which causes the frame 12 to fore-shorten axially and expand radially.

For example, each rod 52 can have external threads that engage internal threads of the nut 56 such that rotation of the rod causes corresponding axial movement of the nut 56 toward or away from the sleeve 54 (depending on the direction of rotation of the rod 52). This causes the hinges supporting the sleeve 54 and the nut 56 to move closer towards each other to radially expand the frame or to move farther away from each other to radially compress the frame, depending on the direction of rotation of the rod 52.

In other examples, the actuators 50 can be reciprocating type actuators configured to apply axial directed forces to the frame to produce radial expansion and compression of the frame. For example, the rod 52 of each actuator can be fixed axially relative to the nut 56 and slidable relative to the sleeve 54. Thus, in this manner, moving the rod 52 distally relative to the sleeve 54 and/or moving the sleeve 54 proximally relative to the rod 52 radially compresses the frame. Conversely, moving the rod 52 proximally relative to the sleeve 54 and/or moving the sleeve 54 distally relative to the rod 52 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a sub-component of the actuators themselves.

Each rod 52 can include an attachment member 58 along a proximal end portion of the rod 52 configured to form a releasable connection with a corresponding actuator of a delivery apparatus. The actuator(s) of the delivery apparatus can apply forces to the rods for radially compressing or expanding the prosthetic valve 10. The attachment member 58 in the illustrated configuration comprises a notch 60 and a projection 62 that can engage a corresponding projection of an actuator of the delivery apparatus.

In the illustrated examples, the prosthetic valve 10 includes three such actuators 50, although a greater or fewer number of actuators could be used in other examples. The leaflets 20 can have commissure attachments members 64 that wrap around the sleeves 54 of the actuators 50. Further details of the actuators, locking mechanisms and delivery apparatuses for actuating the actuators can be found in U.S. Pat. Nos. 10,603,165 and 10,806,573, and 11,135,056, and International Application nos. PCT/US2020/057691 and PCT/US2021/022467, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

The prosthetic valve 10 can include one or more skirts or sealing members. In some examples, the prosthetic valve 10 can include an inner skirt (not shown) mounted on the inner surface of the frame. The inner skirt can function as a sealing member to prevent or decrease perivalvular leakage, to anchor the leaflets to the frame, and/or to protect the leaflets against damage caused by contact with the frame during crimping and during working cycles of the prosthetic valve. As shown in FIG. 1, the prosthetic valve 10 can also include an outer skirt 70 mounted on the outer surface of the frame 12. The outer skirt 70 can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials, including fabrics (e.g., polyethylene terephthalate fabric) or natural tissue (e.g., pericardial tissue). Further details regarding the use of skirts or sealing members in prosthetic valve can be found, for example, in U.S. Pat. No. 11,399,932, which is incorporated herein by reference in its entirety.

FIG. 2 illustrates a delivery apparatus 100, according to one example, adapted to deliver a prosthetic heart valve 102, such as the illustrated prosthetic heart valve 10, described above. The prosthetic valve 102 can be releasably coupled to the delivery apparatus 100. It should be understood that the delivery apparatus 100 and other delivery apparatuses disclosed herein can be used to implant prosthetic devices other than prosthetic valves, such as stents or grafts.

The delivery apparatus 100 in the illustrated example generally includes a handle 104, a first elongated shaft 106 (which comprises an outer shaft in the illustrated example) extending distally from the handle 104, at least one actuator assembly 108 extending distally through the outer shaft 106. The at least one actuator assembly 108 can be configured to radially expand and/or radially collapse the prosthetic valve 102 when actuated.

Though the illustrated example shows two actuator assemblies 108 for purposes of illustration, it should be understood that one actuator 108 can be provided for each actuator on the prosthetic valve. For example, three actuator assemblies 108 can be provided for a prosthetic valve having three actuators. In other examples, a greater or fewer number of actuator assemblies can be present.

In some examples, a distal end portion 116 of the shaft 106 can be sized to house the prosthetic valve in its radially compressed, delivery state during delivery of the prosthetic valve through the patient's vasculature. In this manner, the distal end portion 116 functions as a delivery sheath or capsule for the prosthetic valve during delivery, The actuator assemblies 108 can be releasably coupled to the prosthetic valve 102. For example, in the illustrated example, each actuator assembly 108 can be coupled to a respective actuator of the prosthetic valve 102. Each actuator assembly 108 can comprise a support tube, an actuator member, and a locking tool. When actuated, the actuator assembly can transmit pushing and/or pulling forces to portions of the prosthetic valve to radially expand and collapse the prosthetic valve as previously described. The actuator assemblies 108 can be at least partially disposed radially within, and extend axially through, one or more lumens of the outer shaft 106. For example, the actuator assemblies 108 can extend through a central lumen of the shaft 106 or through separate respective lumens formed in the shaft 106.

The handle 104 of the delivery apparatus 100 can include one or more control mechanisms (e.g., knobs or other actuating mechanisms) for controlling different components of the delivery apparatus 100 in order to expand and/or deploy the prosthetic valve 102. For example, in the illustrated example the handle 104 comprises first, second, and third knobs 110, 112, and 114.

The first knob 110 can be a rotatable knob configured to produce axial movement of the outer shaft 106 relative to the prosthetic valve 102 in the distal and/or proximal directions in order to deploy the prosthetic valve from the delivery sheath 116 once the prosthetic valve has been advanced to a location at or adjacent the desired implantation location with the patient's body. For example, rotation of the first knob 110 in a first direction (e.g., clockwise) can retract the sheath 116 proximally relative to the prosthetic valve 102 and rotation of the first knob 110 in a second direction (e.g., counter-clockwise) can advance the sheath 116 distally. In other examples, the first knob 110 can be actuated by sliding or moving the knob 110 axially, such as pulling and/or pushing the knob. In other examples, actuation of the first knob 110 (rotation or sliding movement of the knob 110) can produce axial movement of the actuator assemblies 108 (and therefore the prosthetic valve 102) relative to the delivery sheath 116 to advance the prosthetic valve distally from the sheath 116.

The second knob 112 can be a rotatable knob configured to produce radial expansion and/or contraction of the prosthetic valve 102. For example, rotation of the second knob 112 can move the actuator member and the support tube axially relative to one another. Rotation of the second knob 112 in a first direction (e.g., clockwise) can radially expand the prosthetic valve 102 and rotation of the second knob 112 in a second direction (e.g., counter-clockwise) can radially collapse the prosthetic valve 102. In other examples, the second knob 112 can be actuated by sliding or moving the knob 112 axially, such as pulling and/or pushing the knob.

The third knob 114 can be a rotatable knob configured to retain the prosthetic heart valve 102 in its expanded configuration. For example, the third knob 114 can be operatively connected to a proximal end portion of the locking tool of each actuator assembly 108. Rotation of the third knob in a first direction (e.g., clockwise) can rotate each locking tool to advance the locking nuts to their distal positions to resist radial compression of the frame of the prosthetic valve, as described above. Rotation of the knob 114 in the opposite direction (e.g., counterclockwise) can rotate each locking tool in the opposite direction to decouple each locking tool from the prosthetic valve 102. In other examples, the third knob 114 can be actuated by sliding or moving the third knob 114 axially, such as pulling and/or pushing the knob.

Although not shown, the handle 104 can include a fourth rotatable knob operative connected to a proximal end portion of each actuator member. The fourth knob can be configured to rotate each actuator member, upon rotation of the knob, to unscrew each actuator member from the proximal portion of a respective actuator. As described above, once the locking tools and the actuator members are uncoupled from the prosthetic valve 102, they can be removed from the patient.

Figure 4:
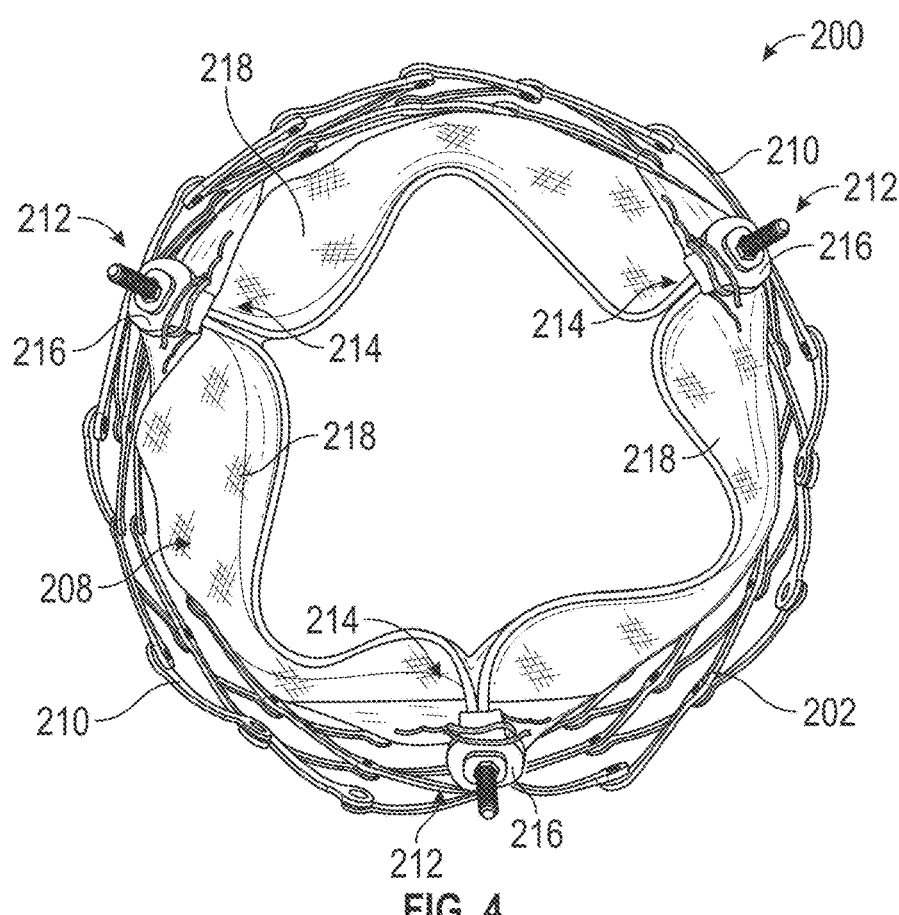
FIG. 4 is a top plan view of the prosthetic heart valve of FIG. 3, with the valvular structure shown in the open configuration.

FIGS. 3-4 illustrate an exemplary example of a prosthetic valve 200 having a frame 202 including an inflow end portion 204 and an outflow end portion 206. The prosthetic valve 200 can further include a leaflet assembly or valvular structure 208, which is coupled to and supported inside the frame 202. The valvular structure 208 is configured to regulate the flow of blood through the prosthetic valve 200 from the inflow end 204 to the outflow end 206.

The prosthetic valve 200 can be similar to prosthetic valve 10, described previously, including a frame 202 (which can be the same or similar to frame 12) comprising a plurality of struts 210 that are pivotably coupled to one another at a plurality of junctions or pivot joints along the length of each strut to form a lattice-type pattern. The frame 202 can comprise one or more actuators or expansion and locking mechanisms 212 mounted to and equally spaced around the inner surface of the frame 202. The expansion and locking mechanisms 212 can be configured to apply expansion and compression forces to the frame for radially expanding and compressing the prosthetic valve. Further details of the expansion and locking mechanisms, including various examples thereof, can be found, for example, in International Application No. PCT/US2020/057691, which is incorporated by reference herein in its entirety.

In some examples, such as the illustrated example, each of the expansion and locking mechanisms 212 can be configured to support a respective commissure 214 (described in more detail below). As such, the expansion and locking mechanisms 212 can comprise commissure support portions 216 (FIG. 4) for supporting and attaching commissures 214 of the valvular structure 208 to the frame 202.

The commissure configurations and attachment methods disclosed herein are described in the context of a mechanically-expandable prosthetic heart valve, such as the valves described in U.S. Pat. No. 10,603,165 and International Application No. PCT/US2021/052745, each of which is incorporated herein by reference. Some mechanical valves can comprise pivotable junctions between the struts, as shown in the illustrated examples, while others can comprise a unitary lattice frame expandable and/or compressible via mechanical means. However, it should be appreciated that the commissure configurations and attachment methods described herein can additionally be used with other types of transcatheter prosthetic valves, including balloon-expandable prosthetic heart valves, such as disclosed in U.S. Pat. Nos. 9,393,110, and 11,096,781, and U.S. Publication No. 2019/0365530, each of which are incorporated herein by reference, and self-expandable prosthetic heart valves, such as disclosed in U.S. Pat. No. 10,098,734, which is incorporated herein by reference.

The valvular structure 208 can include, for example, a leaflet assembly comprising one or more leaflets 218 made of flexible material. The leaflets 218 can be made from in whole or part, biological material, bio-compatible synthetic materials, or other such materials. Suitable biological material can include, for example, bovine pericardium (or pericardium from other sources). As shown in FIG. 4, the leaflets 218 can be secured to one another at their adjacent sides to form commissures 214, and each commissure 214 can be secured to a respective expansion and locking mechanism 212 of the frame 202. In other examples, the commissures 214 can be secured to the frame directly, e.g., to a strut or post of the frame 202.

Figure 5:
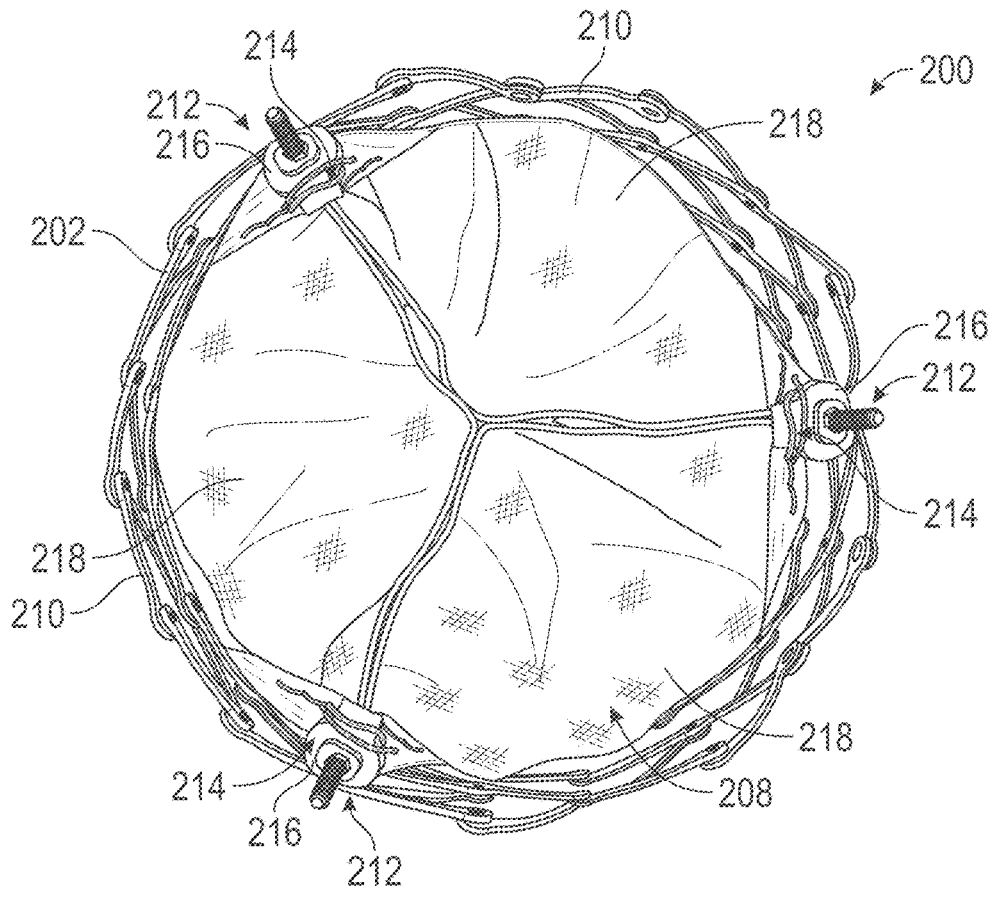
FIG. 5 is a top plan view of the prosthetic heart valve of FIG. 3, with the valvular structure shown in the closed configuration.

In the depicted example, the valvular structure 208 includes three leaflets 218, which can be arranged to collapse in a tricuspid arrangement. That is, the valvular structure 208 can move between an open position (FIG. 4), and a closed position (FIG. 5). In the illustrated example, each leaflet 218 can be coupled to two adjacent leaflets to form three commissures 214, each of which can be secured to a respective expansion and locking mechanism 212 or commissure post.

Figure 6:
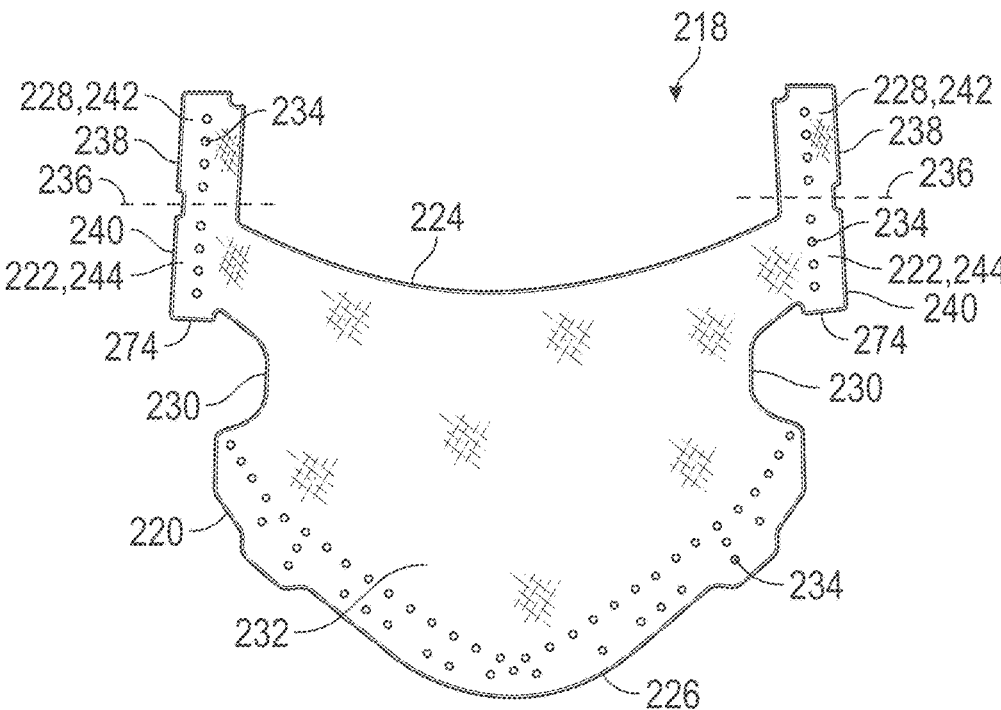
FIG. 6 is a side elevational view of a leaflet of a valvular structure, according to one example.

As shown in FIG. 6, each leaflet 218 can have a cusp edge portion 220. The cusp portions 220 of the leaflets 218 can define an undulating, curved scallop edge that follows or tracks portions of the struts 210 of frame 202 in a circumferential direction when the frame 202 is in the radially expanded configuration. The cusp portions 220 of the leaflets can define a "scallop line" that is attached to a skirt or selected struts of the frame.

The prosthetic valve 200 can further include one or more skirts or sealing members. For example, as shown in FIG. 3, the inflow edge portions 220 of the leaflets 218 can be attached to an inner skirt 221, such as with sutures 225, generally along the scallop line. The inner skirt 221 can in turn be sutured to adjacent struts 210 of the frame 202, for example, via one or more sutures 223 extending around the struts 210. The inner skirt 221 can function as a sealing member to prevent or mitigate perivalvular leakage, to anchor the leaflets 218 to the frame 202, and/or to protect the leaflets against damage caused by contact with the frame during crimping and during working cycles of the prosthetic valve. In other examples, the leaflets 218 can be sutured directly to the frame 202 along the scallop line. In some examples, the prosthetic valve can further comprise an outer skirt mounted on the radially outer surface of the frame 202 (e.g., outer skirt 70).

Referring again to FIG. 6, as mentioned, each leaflet 218 can have a curved, scalloped cusp portion 220 extending between first and second integral lower tabs 222 and an outflow edge 224 (also referred to as a coaptation edge) that contacts (coapts with) respective outflow edges 224 of the other leaflets during diastole. The cusp edge portion 220 can include an inflow edge 226 offset from the outflow edge 224 along a longitudinal axis of the prosthetic valve 200. Each lower tab 222 can be paired with a respective integral upper tab 228 extending axially past the outflow edge 224 of the leaflet 218 when the valvular structure 208 is in a disassembled configuration.

As shown in the illustrated example, each leaflet 218 further can further comprise gaps or recesses 230 in the main body 232 of the leaflet 218. The recesses 230 can be disposed between the lower tabs 222 and the inflow edge 226 of the leaflet 218 and can extend laterally into the main body 232. In some examples, each leaflet 218 can further comprise one or more preformed apertures or openings 234 extending through a thickness of the leaflet 218 for use in assembling the prosthetic valve. One or more sutures can be threaded through the openings 234 secure portions of the leaflet 218 to various other components or to itself.

Figure 7:
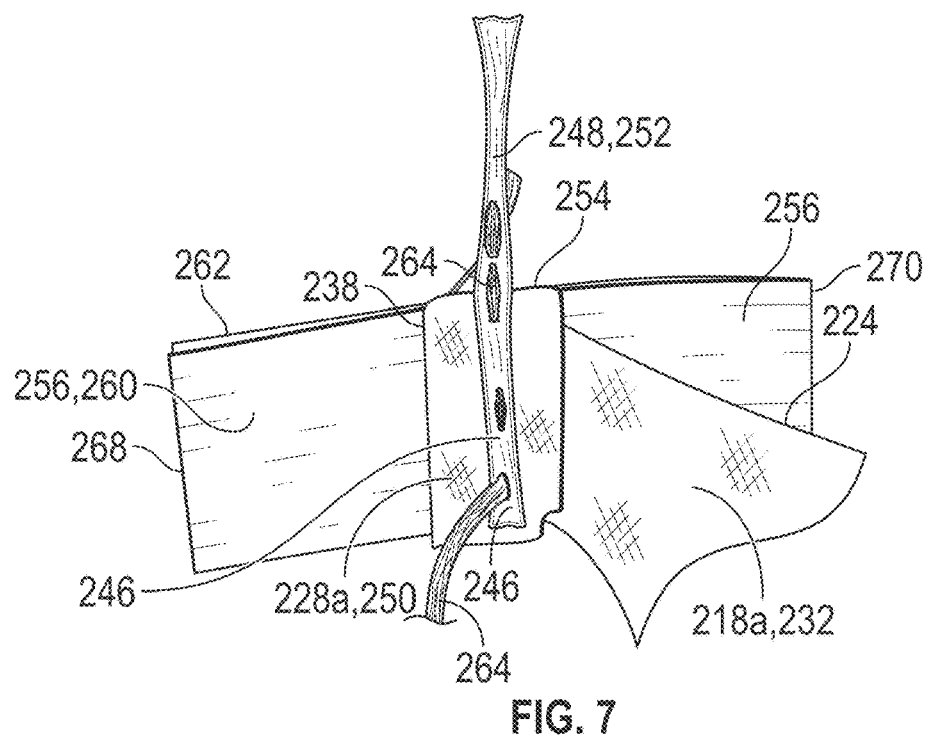
FIGS. 7-14 are perspective views of a portion of a commissure being assembled, according to one example.

FIGS. 7-16 show an exemplary method for assembling a leaflet assembly or valvular structure 208 and mounting the valvular structure 208 to the frame 202. During assembly, the upper tab 228a of a first leaflet 218a can be folded along a fold line 236 (FIG. 6) such that a laterally outer edge 238 of the upper tab 228a substantially aligns with the laterally outer edge 240 of a respective lower tab 222a and such that a first surface 242 of the upper tab 228a contacts a first surface 244 of the lower tab 222a, as shown in FIG. 7. So aligned, a first end portion 246 of a reinforcing member 248 can be disposed on the second surface 250 of the respective upper tab 228a. The second end portion 252 of the reinforcing member 248 can extend past an outflow edge 254 of the tabs 222, 228 and be referred to as a "free end portion."

Figure 8:
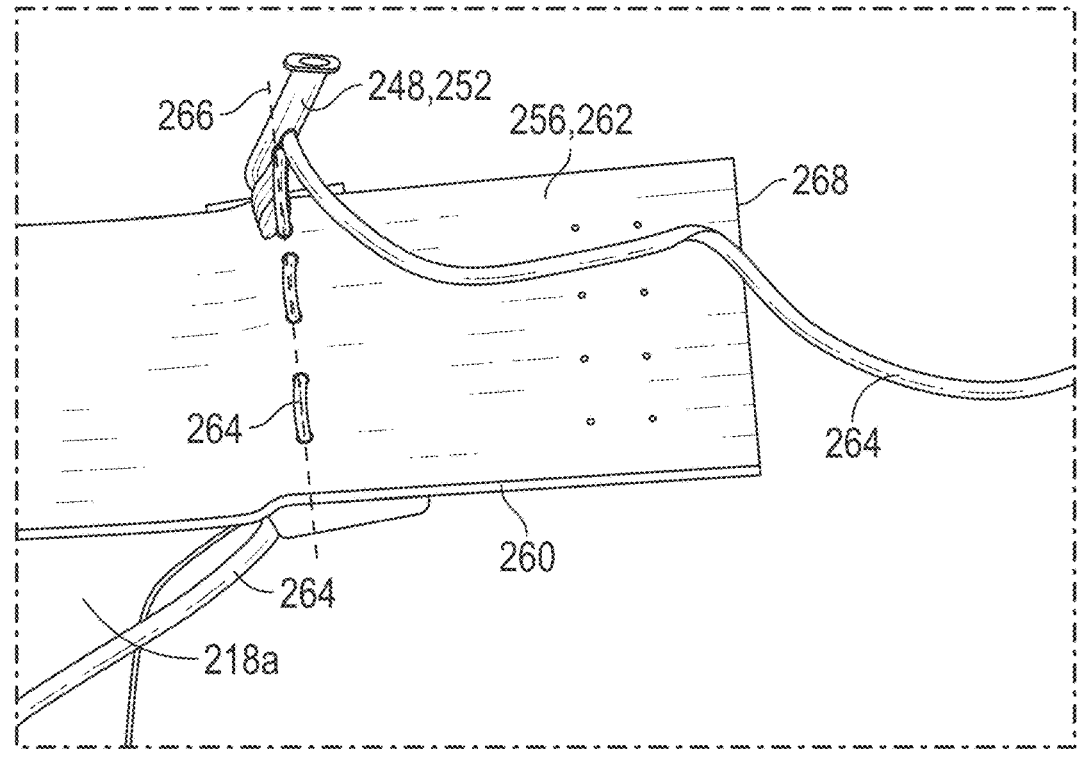
Figure 9:
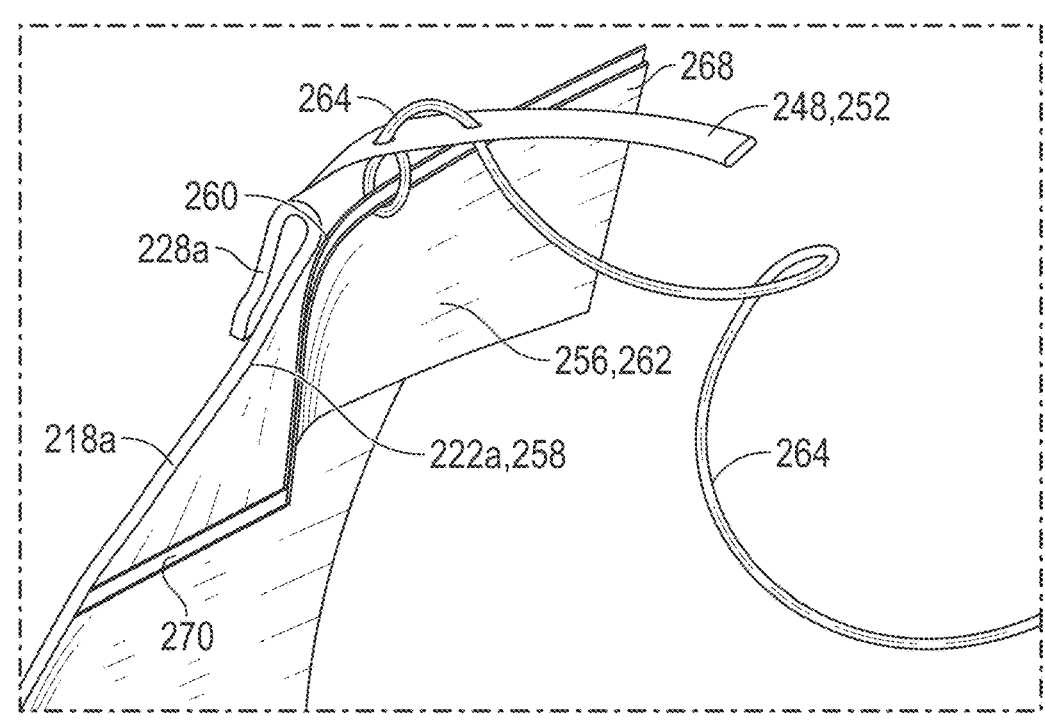

A flexible connector or commissure member 256 can be disposed on the second surface 258 (FIG. 9) of the lower tab 222a. Prior to being attached to a pair of leaflets, the commissure member 256 can comprise one or more layers. For example, in the illustrated example as shown in FIGS. 7-9, the commissure member 256 initially (prior to being attached to the leaflets) includes a first layer 260 and a second layer 262. The first and second layers 260, 262 can be two separate pieces of material of the same size and shape placed side-by-side against each other. For example, in the illustrated example, the first and second layers 260, 262 comprises two separate rectangular pieces of material. In other examples, a single piece of material (e.g., a single rectangular piece of material) can be folded widthwise to form the first and second layers 260, 262. In alternative examples, the commissure member 256 can initially be a single piece of material forming a single layer.

Referring to FIG. 7, a fastening member or suture 264 can be sewn through the reinforcing member 248, the upper tab 228a, the lower tab 222a, and the commissure member 256

Figure 10:
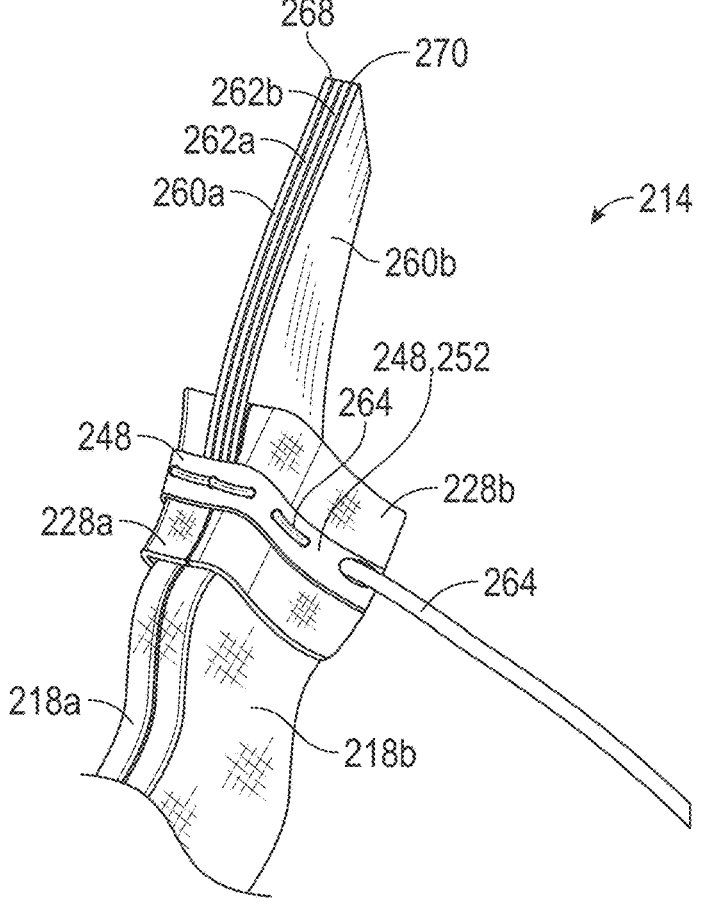

(the first and second layers 260, 262) to couple these components together. The first and second layers of the commissure member 256 can then be folded along a vertical fold line 266 (FIG. 8) such that the first lateral edge 268 of the commissure member 256 is substantially aligned with the second lateral edge 270 of the commissure member to form four layers of the commissure member, as shown in FIG. 10. As shown, after folding, the first layer 260 now forms a first layer 260a and a second layer 260b (which are outer layers of the folded commissure member), and the second layer 262 now forms a third layer 262a and a fourth layer 262b (which are inner layers of the folded commissure member). The third and fourth layers 262a, 262b are sandwiched between the first and second layers 260a, 260b. If the commissure member 256 initially comprises a single layer, then folding the commissure member in this step forms only two layers of the folded commissure member.

The reinforcing member 248 can comprise, for example, one or more multi-filament sutures (e.g., an Ethibond suture) or one or more strips of material, such as cloth or fabric (e.g., polyethylene terephthalate (PET) cloth), including braided cloth (e.g., a flat braid), non-fabric material (e.g., silicon or polyurethane), natural tissue (e.g., pericardium), or metallic components (e.g., a metallic braid or metal strip). The commissure member 256 can similarly comprise a soft and flexible non-metallic material, such as strips of synthetic material, such as fabric (e.g., PET) or non-fabric material (e.g., silicone or polyurethane), or natural tissue (e.g., pericardium).

Referring to FIG. 10, the upper tab 228b of a second leaflet 218b can be folded onto the lower tab 222 as described previously for the first leaflet 218a. The second leaflet 218b can be disposed adjacent the first leaflet 218a such that the commissure member 256 is sandwiched between the lower tabs 222a, 222b of each leaflet 218a, 218b. So disposed, the second end portion 252 of the reinforcing member 248 can be folded over the second upper tab 228b and secured thereto via the fastening suture 264 to form a commissure assembly 214. As shown, the fastening suture 264 can be sewn such that it extends directly through the reinforcing member 248, the lower and upper tabs 222b, 228b of the second leaflet 218b and the second and fourth layers 260b, 262b of the commissure member. The fastening suture 264 can be sewn in an in-and-out pattern (e.g., a running stitch). The suture 264 secures one end portion of the fastening member 248 to the tabs of the first leaflet 218a and layers 260a, 262a with a first set of stitches 265a, and the other end portion of the fastening member 248 to the tabs of the second leaflet 218b and layers 260b, 262b with a second set of stitches 265b (see FIG. 11).

In the illustrated example, the reinforcing member 248 is a single or continuous piece of material that is folded around the upper edges of the leaflets. In other examples, there can be two separate reinforcing members, one of which is sutured to the tabs 222a, 228a of the first leaflet 218a, and the other of which is sutured to the tabs 222b, 228b of the second leaflet 218b.

Figure 11:
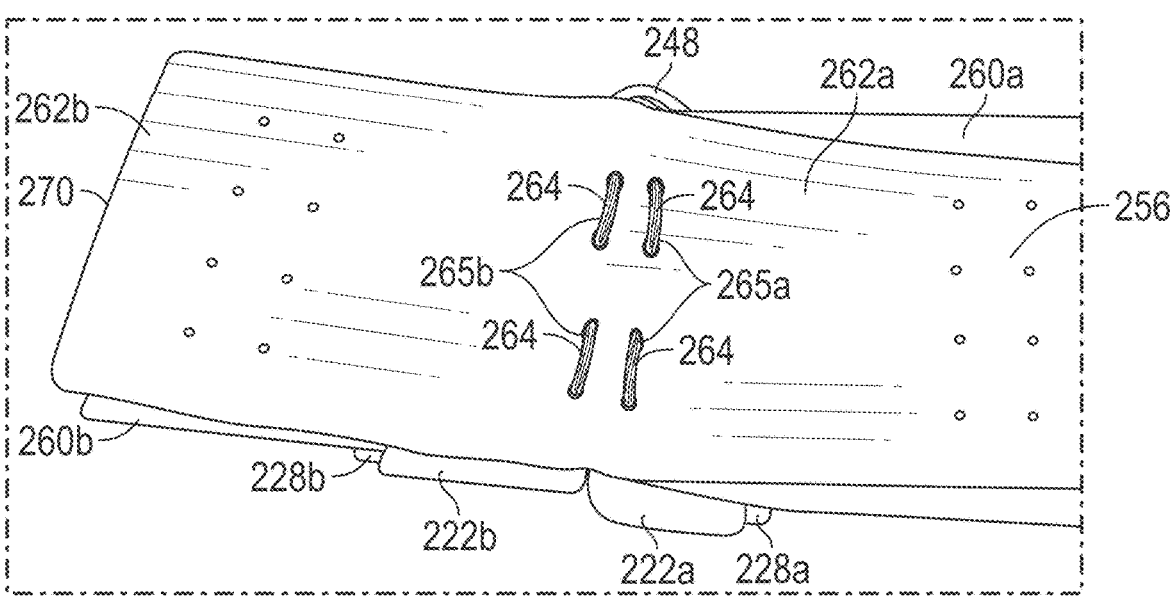
Figure 12:
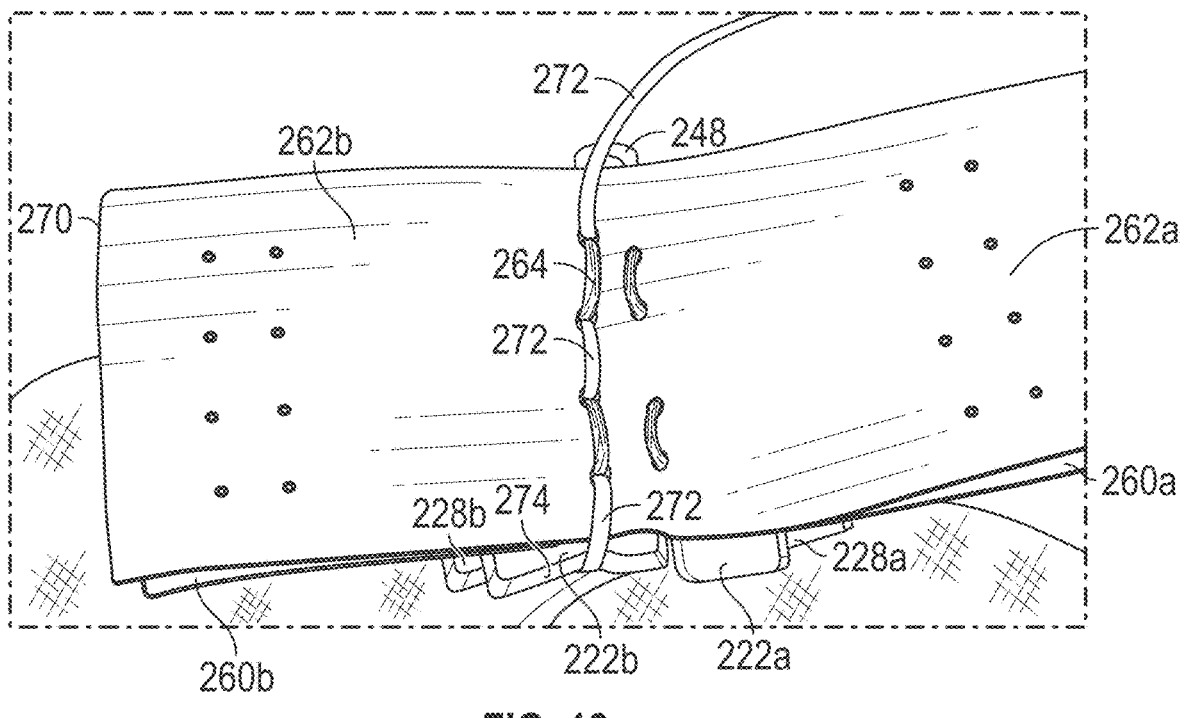

Referring to FIG. 11, the first and third layers 260a and 262a can be pulled apart from the second and fourth layers 260b and 262b such that these layers are substantially perpendicular to the upper and lower tabs of the leaflets. As shown in FIG. 12, one or more additional sutures 272 can then be sewn through layers 262b and 260b, through the lower tab 222b, and the upper tab 228b of the second leaflet 218b. The additional sutures 272 can bias the upper and lower tabs 222a, 228a of the first leaflet 218a away from those of the second leaflet 218b.

Figure 13:
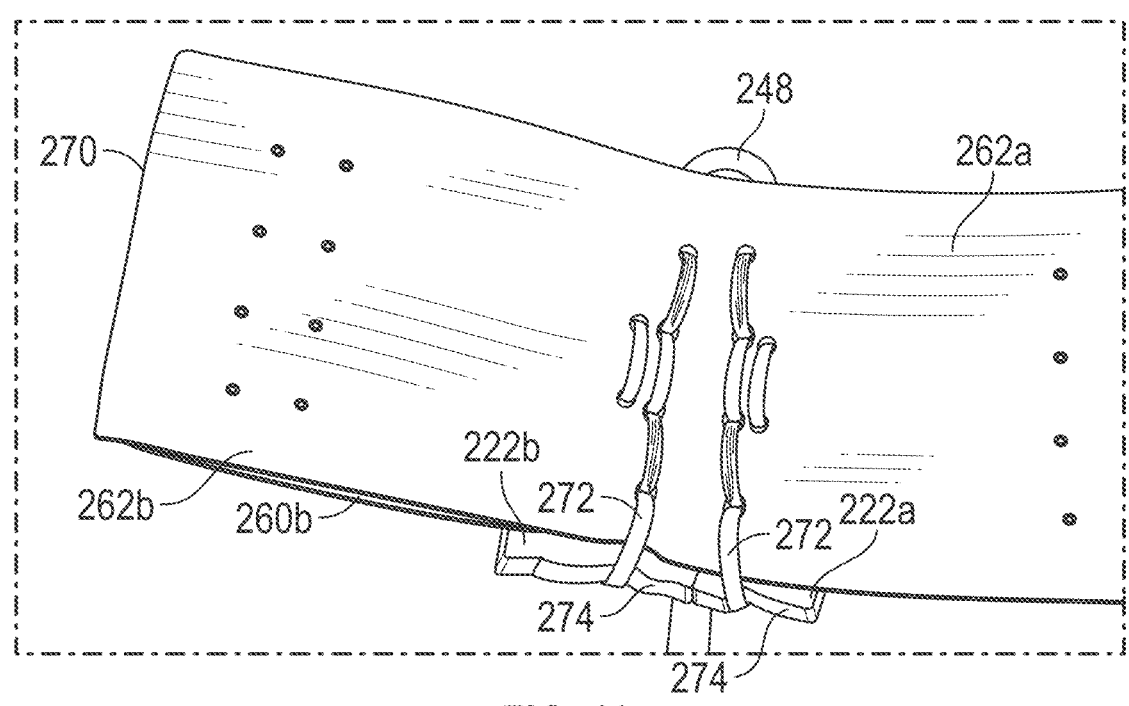

The additional sutures 272 can be sewn in an in-and-out pattern (e.g., a running stitch) that alternates with the running stitch sewn with fastening suture 264, as shown in FIG. 12. The process can then be repeated on the remaining leaflet 218*a*, as shown in FIG. 13 (the sutures 272 form stitches extending through the tabs 222*a*, 228*a* of the first leaflet and layers 260*a*, 262*a*). As shown, the additional sutures 272 can be stitched in-line with and/or adjacent the fastening suture 264. In some examples, the additional sutures 272 can be sewn directly over the fastening suture 264. As shown in FIG. 12, in some examples, the additional suture 272 can wrap around an inflow edge 274 of the lower and upper tabs 222, 228. The additional sutures 272 can provide reinforcement to the connection between the commissure member 256 and the leaflet tabs 222, 228, thereby reinforcing the commissure 214. The additional sutures 272 can be, for example, force fiber sutures, which can be made of high molecular weight polyethylene (UHMWPE).

Figure 14:
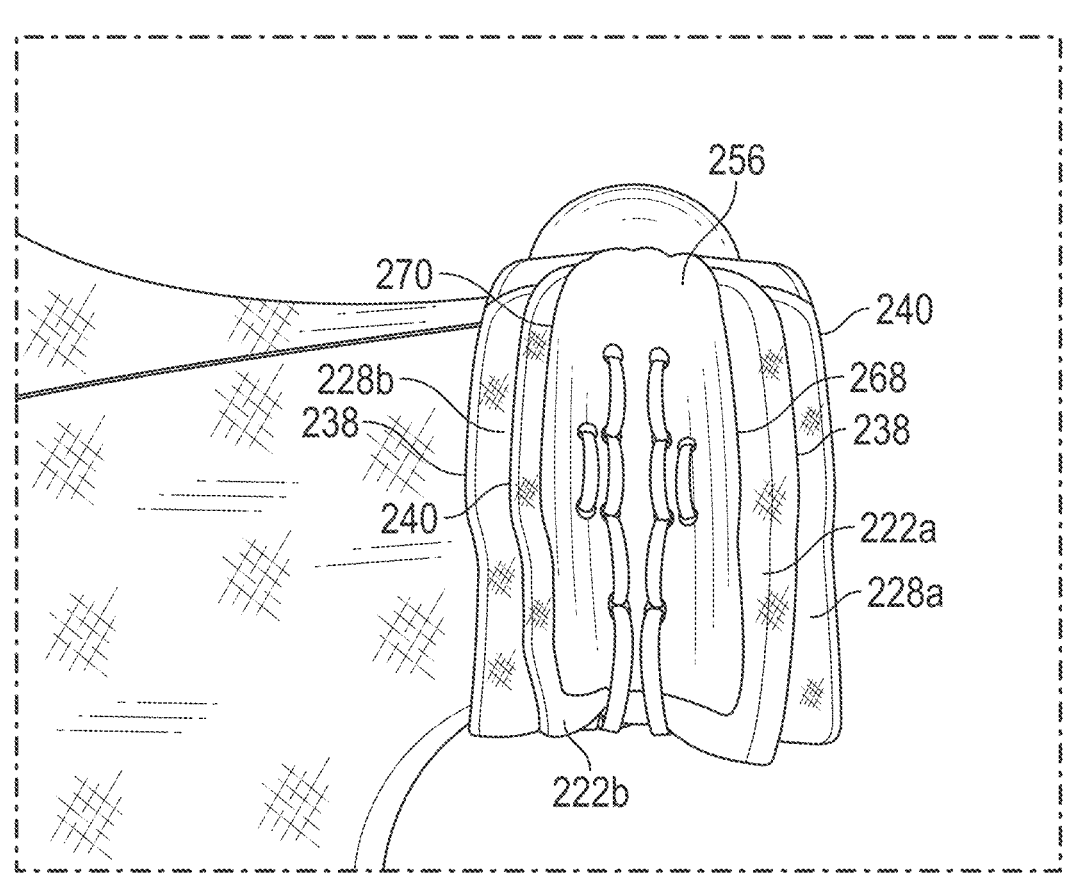

In some examples, the additional sutures 272 can be sewn in a zig-zag pattern such that the additional sutures can serve as both a primary and a secondary suture line. The additional sutures 272 can be configured to bias the laterally outer edges 238, 240 of a respective upper tab 228*b* and lower tab 222*b* pair away from the adjacent upper tab 228*a* and lower tab 222*a* pair, as shown in FIG. 13. As shown in FIG. 14, the lateral edges 268, 270 of the commissure member 256 can be trimmed such that they do not extend past the lateral edges 238, 240 of the upper and lower tabs 228, 222.

Figure 15:
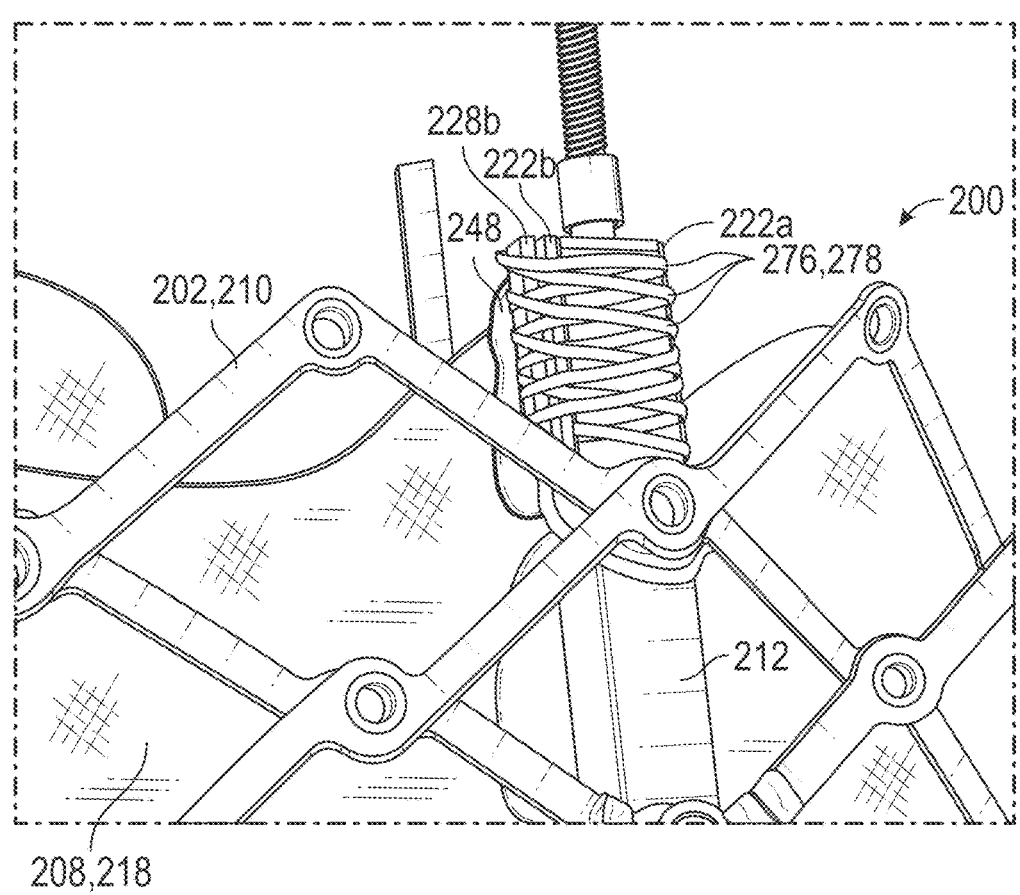
FIG. 15 is a perspective view of the commissure of FIGS. 7-14 coupled to a frame of a prosthetic heart valve, according to one example.
Figure 16:
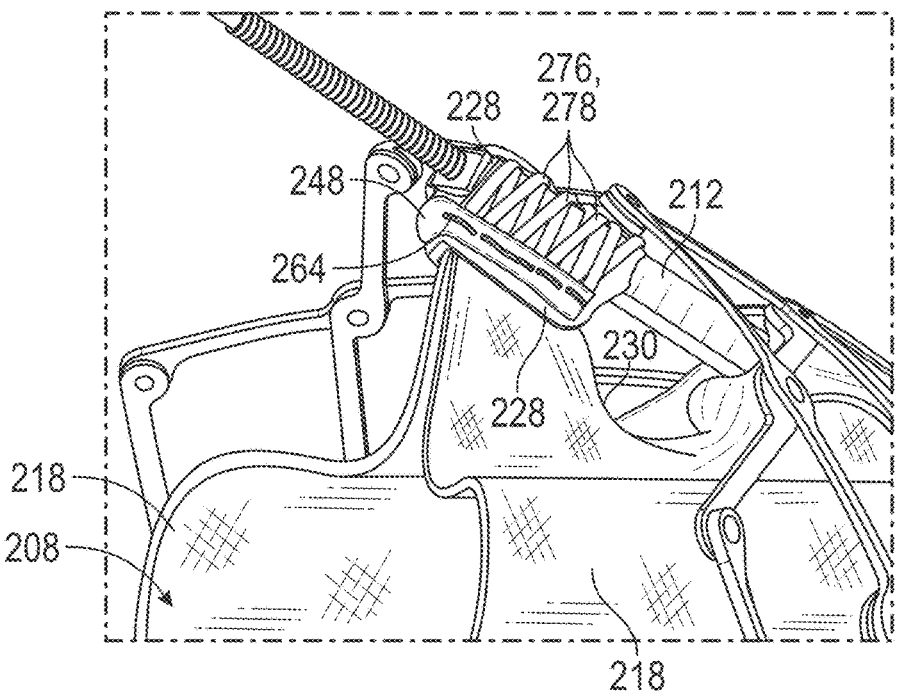
FIG. 16 is a perspective view of a portion of the prosthetic heart valve of FIG. 15.

Referring now to FIG. 15, securing sutures 276 can be sewn through the reinforcing member 248 and around the lateral edges of the lower and upper tabs 222, 228 to form loops 278. The loops 278 can then be slid axially over a respective expansion and locking mechanism 212 (or another component of the frame assembly that forms a commissure post/commissure feature/commissure support) such that the valvular structure 208 is disposed within the circumference of the frame 202. So disposed, the loops 278 can be tightened and tied off to secure the valvular structure to the frame 202, as shown in FIGS. 15-16.

Alternatively, the loops 278 can be formed after placing the tabs of the first leaflet 218*a* on one side of the mechanism 212 and the tabs of the second leaflet 218*b* on the other side of the mechanism 212.

Figure 22:
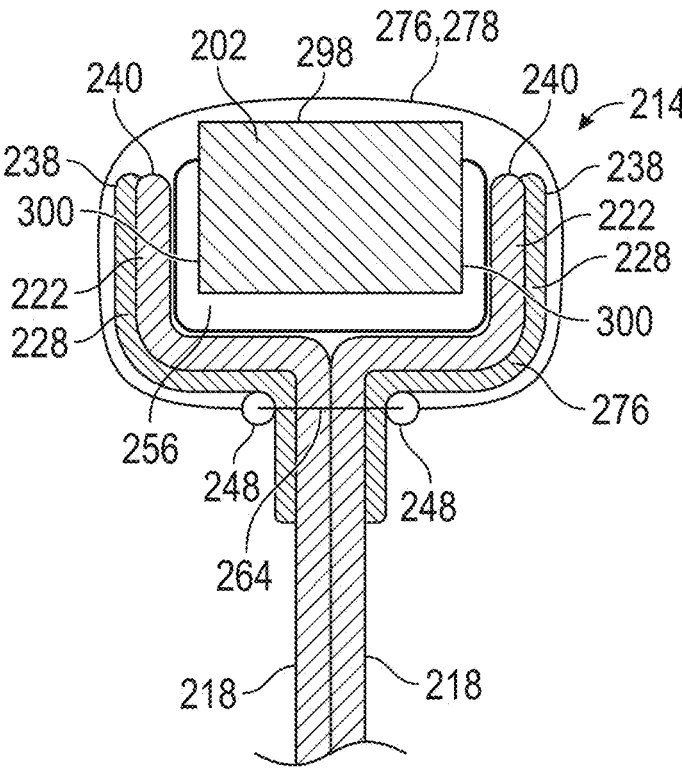
FIG. 22 is a top plan cross-sectional view of an exemplary commissure coupled to the frame of a prosthetic heart valve, according to one example.

FIG. 22 shows a cross-section of the commissure 214 coupled to the frame 202. As shown, the commissure member 256 is disposed between the frame 202 and the lower and upper tabs 222, 228 of each leaflet 218. The reinforcing member 248 is fastened to the leaflets 218 via fastening suture 264 and reinforces the flexural bend of the leaflets 218 to prevent or mitigate wear. As shown, the securing sutures 276 can extend through the reinforcing member 248, around the lateral edges 238, 240 of the tabs 222, 228 and around the radially outer surface 298 of the frame 202. In the illustrated example, the commissure member 256 and tabs 222, 228 extend over the circumferential side surfaces 300 of the frame 202. Positioning the commissure member 256 and tabs 222, 228 between suture loops 278 and the frame 202 can mitigate wear or destruction of the suture loops 278 via frictional engagement with the frame 202.

Figure 23:
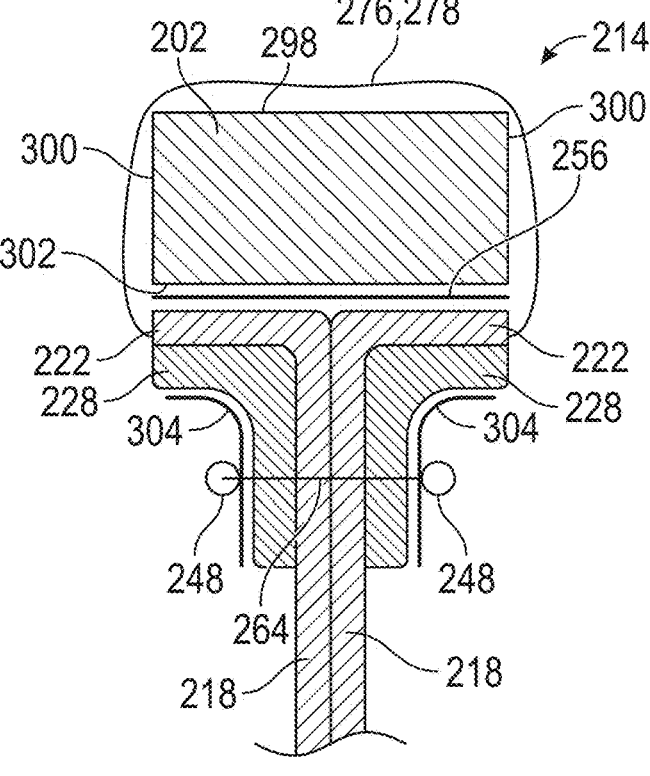
FIG. 23 is a top plan cross-sectional view of an exemplary commissure coupled to the frame of a prosthetic heart valve, according to another example.

In other examples, as shown in FIG. 23, the commissure 214 can be configured in the following manner. Commissure member 256 can be disposed only on the radially inner surface 302 of the frame 202, and the suture loops 278 can be disposed directly adjacent the circumferential side surfaces 300 and the radially outer surface 298 of the frame 202. In some examples, as shown, a cloth or fabric member

304 (e.g., PET fabric) can be disposed between the reinforcing member 248 and the upper tabs 228, to provide additional reinforcement. In some examples, the fabric member can comprise two separate pieces of fabric, one positioned between the upper tab 228*a* of the first leaflet 218*a* and the reinforcing member 248 and the other positioned between the upper tab 228*b* of the second leaflet 218*b* and the reinforcing member 248. In other examples, the fabric member can be a single piece of material that is positioned against the upper tabs 228*a*, 228*b* of the leaflets and folded over the upper edges of the upper tabs 228*a*, 228*b*, similar to the reinforcing member 248.

Figure 24:
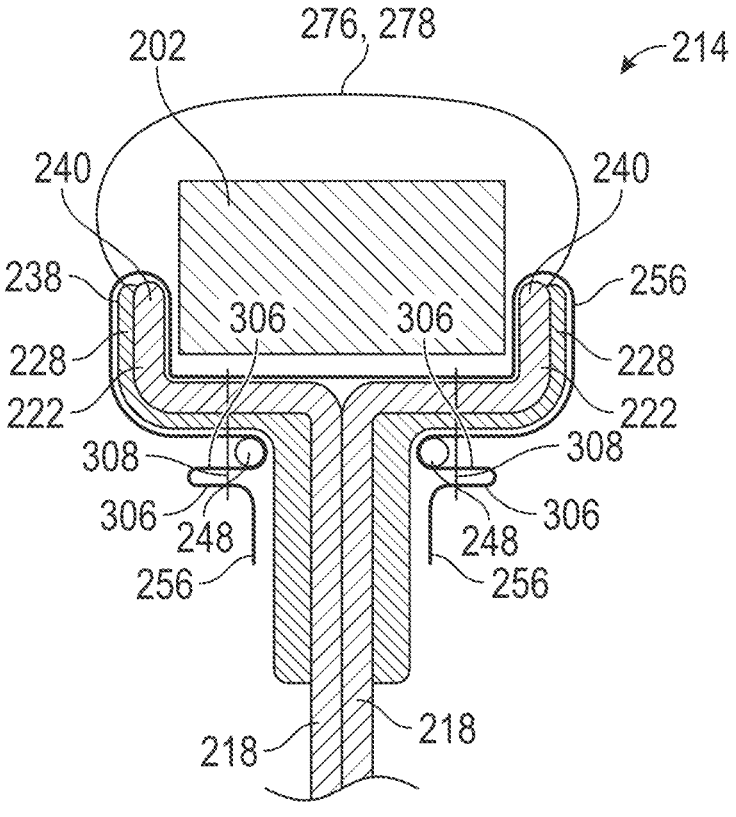
FIG. 24 is a top plan cross-sectional view of an exemplary commissure coupled to the frame of a prosthetic heart valve, according to yet another example.

In still other examples, as shown in FIG. 24, the commissure 214 can be configured as follows. The commissure member 256 can extend between the tabs 222, 228 and the frame 202, around the lateral edges 238, 240 of the tabs 222, 228, and between the tabs 222, 228 and the reinforcing member 248. In some examples, as shown, portions of the commissure member 256 can be folded to form first and second folds 306. Additional sutures 308 can be sewn through the folds 306, the commissure member 256, and the leaflet tabs 222, 228 to secure the components to one another, provide additional reinforcement, and/or keep the leaflets aligned.

The configurations described above can advantageously minimize the amount of cloth material (e.g., such as the commissure member 256) disposed at the commissure 214, thereby preventing or mitigating the risk of commissure fibrosis. Further, the reinforcing member 248 advantageously reinforces the primary loading at the flexural bend of the leaflets. The portion of the leaflets 218 covered by the reinforcing member 248 can be more resistant to bending, or articulating, than the portion of the leaflets 218 just relatively inward from the more rigid reinforced portion. This causes the leaflets 218 to articulate primarily at the inner edges of the reinforcing member 248 in response to blood flowing through the valve during operation within the body, as opposed to articulating at respective axes on or adjacent the metal struts of the frame 202. Because the leaflets 218 articulate at a location spaced radially inwardly of the frame 202, the leaflets can avoid contact with and damage from the frame. This is particularly advantageous in cases where the prosthetic valve is not fully expanded when implanted in a patient's body. As such, the prosthetic valve can be implanted in a wider range of patient annulus sizes.

Prior to attaching the leaflets to the frame, each leaflet can be attached to an adjacent leaflet to form a commissure 214 in the manner described above to form a pre-assembled leaflet assembly. For example, in the illustrated example, the leaflet assembly includes three leaflets 218 and three commissures 214. The leaflet assembly can then be placed inside the frame and each commissure 214 can be attached to a respective commissure post, such as actuator component 212.

Figure 17:
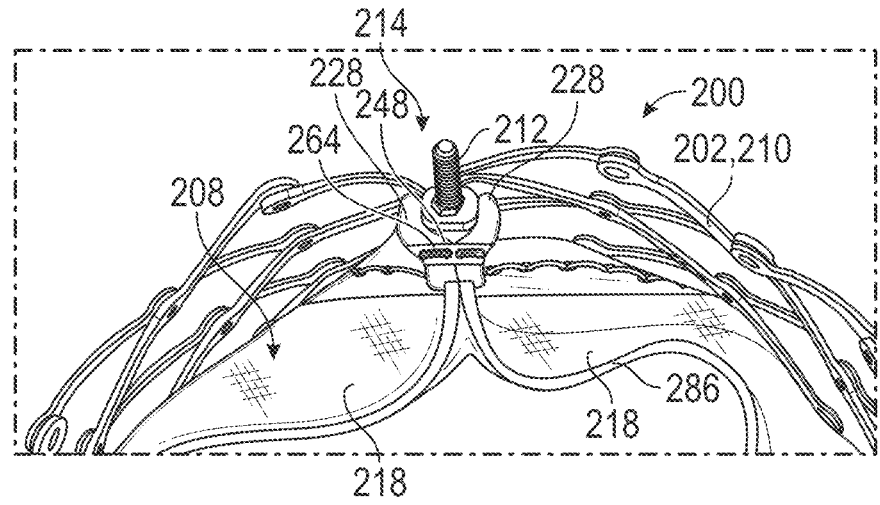
FIG. 17 is a top plan view of a portion of the prosthetic heart valve of FIG. 15.
Figure 18:
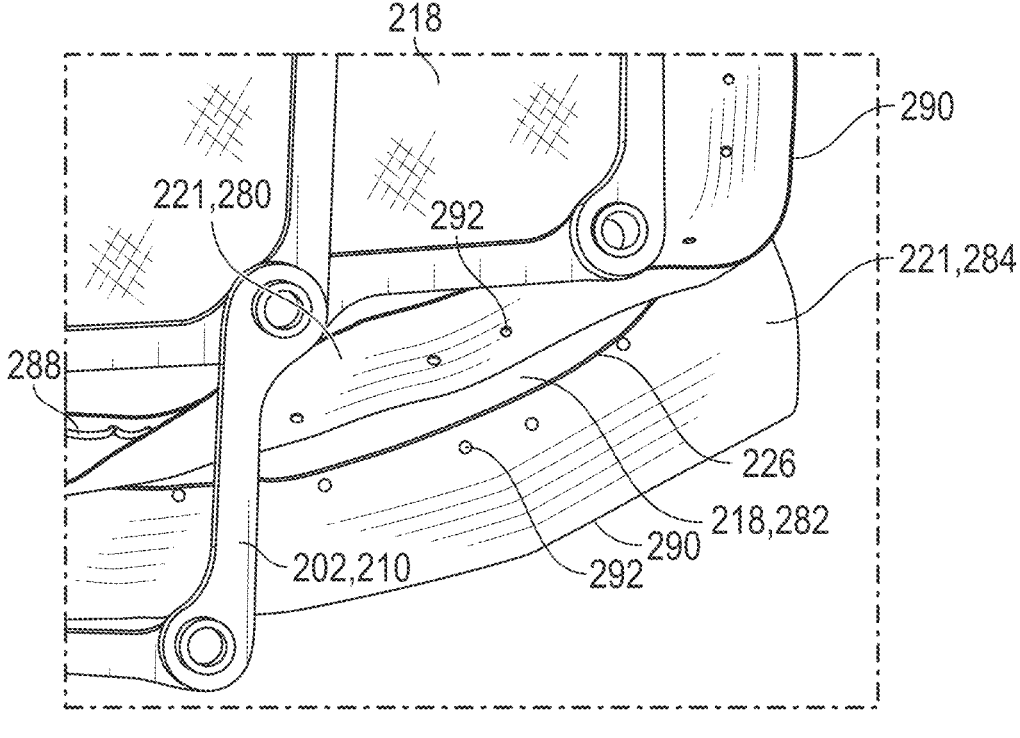
FIG. 18 is a perspective view of a portion of a prosthetic heart valve, according to one example.
Figure 19:
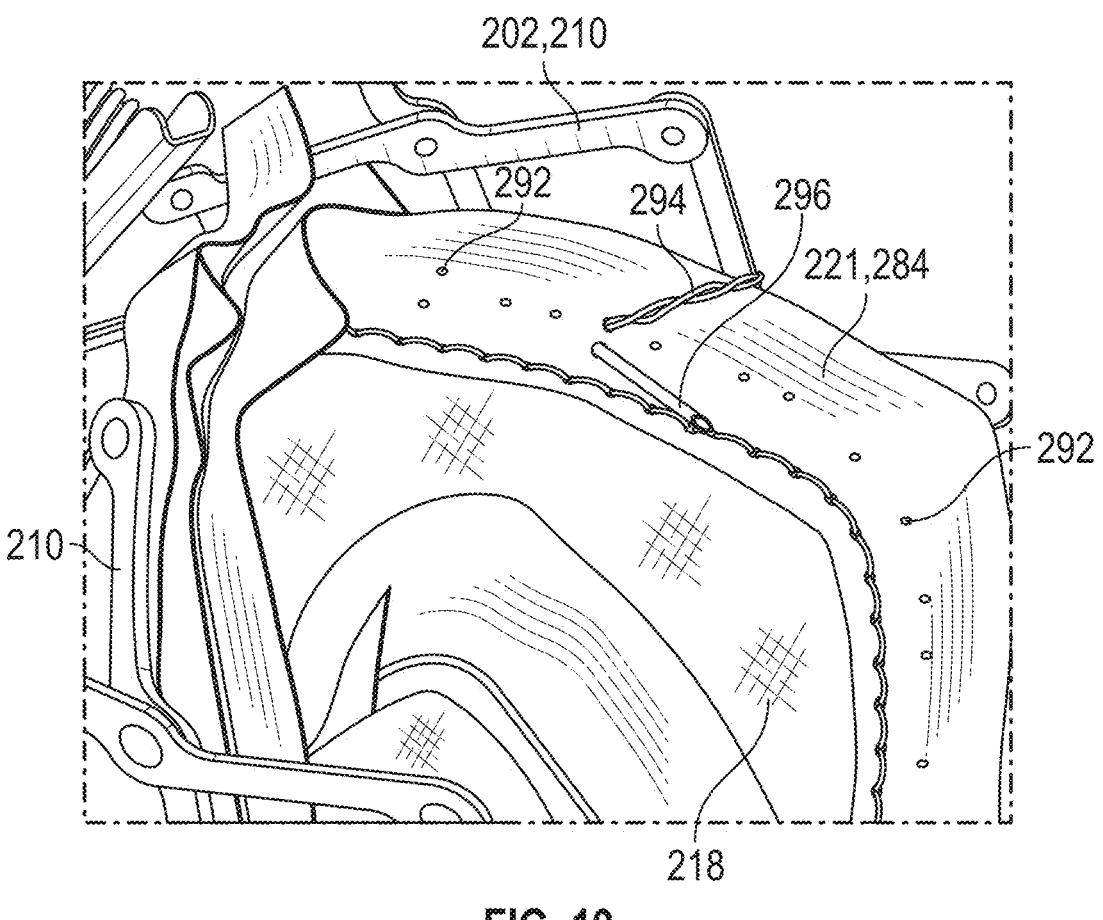
FIG. 19 is a perspective view of the prosthetic heart valve of FIG. 18.
Figure 20:
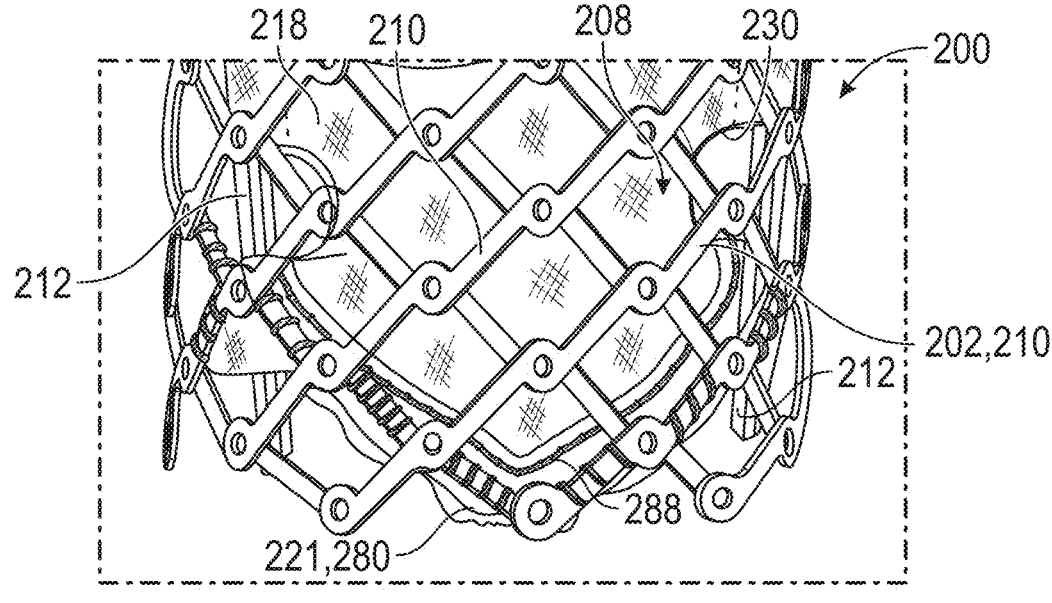
FIG. 20 is a perspective view of the prosthetic heart valve of FIG. 18.
Figure 21:
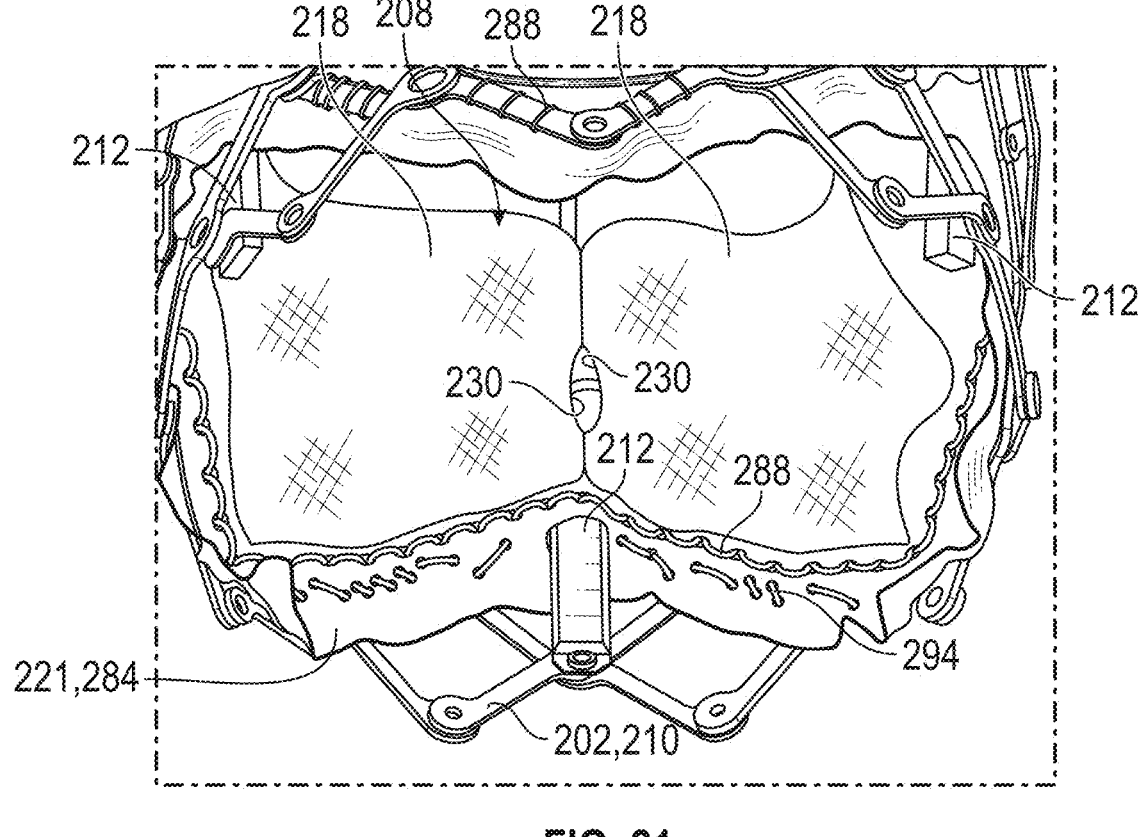
FIG. 21 is a perspective view of the prosthetic heart valve of FIG. 18.

Once the commissures 214 have been secured to respective expansion and locking mechanisms 212 of the frame, the lower edges of the leaflets 218 between the commissures 214 can be sutured to the inner skirt 221. Referring to FIG. 18, the inner skirt 221 can comprise a first layer 280 disposed on a radially outer surface 282 of the leaflet 218, and a second layer 284 disposed on a radially inner surface 286 (FIG. 17) of the leaflet 218. The first and second layers 280, 284 can be sutured to the leaflet 218 using one or more sutures 288 (e.g., Ethibond sutures) along a suture line, such that the inflow edges 290 of the first and second layers 280, 284 extend past the inflow edge 226 of the leaflet 218. The suture 288 can be sewn in an in-and-out pattern (e.g., a running stitch) extending through the first layer 280, the leaflet 218, and the second layer 284.

The first and second layers 280, 284 of the inner skirt 221 can comprise preformed openings 292 through which a fastening suture 294 can be sewn. For example, the fastening suture 294 can be coupled to a needle 296 and can be sewn such that it extends through the second layer 284, leaflet 218, first layer 280, around a respective strut 210, then back through the first layer 280, leaflet 218, and second layer 284, in an in-and-out pattern (e.g., a running stitch). One or more fastening sutures 294 can secure the leaflets 218 and inner skirt 221 to the frame 202 about the circumference of the frame.

Though the previously-described examples are described with reference to a mechanically-expandable prosthetic valve, it should be noted that commissure assemblies and skirt assemblies such as those previously-described can be used with any type of prosthetic valve, for example, self-expanding or balloon-expandable valves.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A method of assembling a valvular structure, comprising:

folding an integral upper tab of a first leaflet onto an integral lower tab of the first leaflet such that a first surface of the upper tab contacts a first surface of the lower tab;

disposing a first end portion of a reinforcing member on a second surface of the upper tab of the first leaflet;

disposing a commissure member adjacent a second surface of the lower tab of the first leaflet;

coupling the first end portion of the reinforcing member, the upper and lower tabs of the first leaflet, and the commissure member to one another using one or more fastening sutures;

folding an integral upper tab of a second leaflet onto an integral lower tab of the second leaflet such that a first surface of the upper tab contacts a first surface of the lower tab;

disposing the second leaflet adjacent the first leaflet such that the commissure member is positioned between the respective lower tabs;

disposing a second end portion of the reinforcing member on a second surface of the upper tab of the second leaflet; and coupling the second end portion of the reinforcing member, the upper and lower tabs of the second leaflet, and the commissure member to one another using the one or more fastening sutures to form a commissure.

Example 2. The method of any example herein, particularly example 1, further comprising prior to disposing the second leaflet adjacent the first leaflet, folding the commissure member such that first and second lateral edges of the commissure member are disposed adjacent one another.

Example 3. The method of any example herein, particularly any one of examples 1-2, further comprising cutting back the first and second lateral edges of the commissure member such that they do not extend past lateral edges of the upper and lower tabs of the first and second leaflets.

Example 4. The method of any example herein, particularly any one of examples 1-3, wherein the one or more fastening sutures extend through the first end portion and the second end portion of the reinforcing member.

Example 5. The method of any example herein, particularly any one of examples 1-4, wherein the commissure member comprises first and second layers.

Example 6. The method of any example herein, particularly any one of examples 1-5, further comprising sewing one or more securing sutures through the commissure such that they extend around the lateral edges of the upper and lower tabs of the first and second leaflets to form a plurality of loops, sliding the plurality of loops axially over a commissure support portion of an expansion and locking mechanism coupled to a frame of a prosthetic heart valve such that the leaflets are disposed within the frame, and tightening the plurality of loops to secure the leaflets to the frame.

Example 7. The method of any example herein, particularly example 6, wherein sewing one or more securing sutures through the commissure comprises sewing the securing sutures through the reinforcing member.

Example 8. The method of any example herein, particularly example 6, wherein sewing one or more securing sutures through the commissure comprises sewing the securing sutures through the lateral edges of the upper and lower tabs of the first and second leaflets.

Example 9. The method of any example herein, particularly any one of examples 1-8, further comprising sewing one or more additional sutures through the commissure member to bias the upper and lower tabs of the first and second leaflets away from one another.

Example 10. The method of any example herein, particularly example 9, wherein one or more stitches of the additional sutures are stitched in-line with the one or more fastening sutures.

Example 11. The method of any example herein, particularly example 10, wherein the one or more stitches of the additional sutures are sewn directly over the one or more fastening sutures.

Example 12. The method of any example herein, particularly example 10, wherein the one or more stitches of the additional sutures are sewed in an alternating pattern with one or more stitches of the one or more fastening sutures.

Example 13. The method of any example herein, particularly any one of examples 9-12, wherein one or more stitches of the additional sutures are disposed laterally adjacent to one or more stitches of the one or more fastening sutures.

Example 14. The method of any example herein, particularly any one of examples 9-13, wherein one or more stitches of the additional sutures wrap around an inflow edge of the upper and lower tabs.

Example 15. The method of any example herein, particularly any one of examples 1-14, wherein the integral upper and lower tabs of each leaflet are first integral upper and lower tabs, and wherein each leaflet further comprises second integral upper and lower tabs arranged at an opposing end of a cusp edge portion of the leaflet.

Example 16. The method of any example herein, particularly any one of examples 1-15, wherein the reinforcing member comprises at least one of multi-filament suture, braided cloth, metallic braid, and metal strip.

Example 17. The method of any example herein, particularly any one of examples 1-16, wherein the reinforcing member comprises an Ethibond suture.

Example 18. The method of any example herein, particularly any one of examples 1-17, wherein the commissure member comprises PET.

Example 19. The method of any example herein, particularly any one of examples 1-18, wherein the reinforcing member is radially inset from the lateral edges of the upper and lower tabs of the first and second leaflets.

Example 20. The method of any example herein, particularly any one of examples 1-19, wherein the valvular structure comprises three leaflets, each coupled one or more adjacent leaflets at a respective commissure.

Example 21. A method of assembling a prosthetic heart valve including a valvular structure, comprising:

disposing a first end portion of a reinforcing member an upper tab of a first leaflet, the upper tab disposed over a respective lower tab;

disposing a commissure member adjacent the lower tab of the first leaflet, the commissure member folded to form first and second layers;

coupling the first end portion of the reinforcing member, the upper and lower tabs of the first leaflet, and the commissure member to one another using one or more fastening sutures;

disposing a second leaflet adjacent the first leaflet such that the first and second layers of the commissure member are positioned between a lower tab of the second leaflet and the lower tab of the first leaflet;

disposing a second end portion of the reinforcing member on an upper tab of the second leaflet;

coupling the second end portion of the reinforcing member, the upper and lower tabs of the second leaflet, and the commissure member to one another using the one or more fastening sutures to form a commissure;

cutting first and second lateral portions of the commissure member such that lateral edges of the commissure member do not extend past lateral edges of the upper and lower tabs of the first and second leaflets;

sewing one or more securing sutures through the commissure such that they extend around lateral edges of the upper and lower tabs of the first and second leaflets to form a plurality of loops;

sliding the plurality of loops axially over a commissure support portion of a frame of the prosthetic valve such that the leaflets are disposed within the frame; and tightening the plurality of loops to secure the leaflets to the frame.

Example 22. The method of any example herein, particularly example 21, wherein the first and second layers of the commissure member each comprise an inner layer and an outer layer.

Example 23. The method of any example herein, particularly any one of examples 21-22, wherein the commissure support portion is an expansion and locking mechanism.

Example 24. The method of any example herein, particularly any one of examples 21-23, wherein sewing one or more securing sutures through the commissure comprises sewing the securing sutures through the reinforcing member.

Example 25. The method of any example herein, particularly example 24, wherein the securing sutures extend through the first end portion and second end portion of the reinforcing member.

Example 26. The method of any example herein, particularly any one of examples 21-25, wherein sewing one or more securing sutures through the commissure comprises sewing the securing sutures through the lateral edges of the upper and lower tabs of the first and second leaflets.

Example 27. The method of any example herein, particularly any one of examples 21-26, wherein the valvular structure comprises three leaflets, each coupled one or more adjacent leaflets at a respective commissure.

Example 28. The method of any example herein, particularly any one of examples 21-27, wherein the reinforcement member comprises at least one of multi-filament suture, braided cloth, metallic braid, and metal strip.

Example 29. The method of any example herein, particularly any one of examples 21-28, wherein the reinforcing member comprises an Ethibond suture.

Example 30. The method of any example herein, particularly any one of examples 21-29, wherein the commissure member comprises PET.

Example 31. The method of any example herein, particularly any one of examples 21-30, wherein the reinforcing member is radially inset from the lateral edges of the upper and lower tabs of the first and second leaflets.

Example 32. The method of any example herein, particularly any one of examples 21-31, wherein the integral upper and lower tabs of each leaflet are first integral upper and lower tabs, and wherein each leaflet further comprises second integral upper and lower tabs arranged at an opposing end of a cusp edge portion of the leaflet.

Example 33. The method of any example herein, particularly any one of examples 21-32, further comprising sewing one or more additional sutures through the commissure member to bias the upper and lower tabs of the first and second leaflets away from one another.

Example 34. The method of any example herein, particularly example 33, wherein one or more stitches of the additional sutures are stitched in-line with the one or more fastening sutures.

Example 35. The method of any example herein, particularly any one of examples 33-34, wherein the one or more stitches of the additional sutures are sewn directly over the one or more fastening sutures.

Example 36. The method of any example herein, particularly example 35, wherein the one or more stitches of the additional sutures are sewed in an alternating pattern with one or more stitches of the one or more fastening sutures.

Example 37. The method of any example herein, particularly any one of examples 33-36, wherein one or more stitches of the additional sutures are disposed laterally adjacent to the one or more fastening statures.

Example 38. The method of any example herein, particularly any one of examples 33-36, wherein one or more stitches of the additional sutures wrap around an inflow edge of the upper and lower tabs.

Example 39. A prosthetic heart valve, comprising:

a radially expandable and compressible annular frame comprising a plurality of expansion and locking mechanisms;

a valvular structure comprising a plurality of commissures, each commissure comprising:

a first leaflet having an integral upper tab and an integral lower tab, the upper tab being folded over the lower tab, a second leaflet having an integral upper tab and an integral lower tab, the upper tab being folded over the lower tab, a commissure member disposed between the lower tabs of the first and second leaflets;

a reinforcing member having a first end portion disposed on the upper tab of the first leaflet and a second end portion disposed on the upper tab of the second leaflet; and wherein each commissure is coupled to a respective expansion and locking mechanism via a plurality of loops coupled to the commissure and extending around the expansion and locking mechanism, such that the valvular structure is disposed within and supported by the frame.

Example 40. The prosthetic heart valve of any example herein, particularly example 39, wherein the integral upper and lower tabs of the first leaflet are first integral upper and lower tabs, and wherein the first leaflet further comprises second integral upper and lower tabs arranged at an opposing end of a cusp edge portion of the leaflet.

Example 41. The prosthetic heart valve of any example herein, particularly any one of examples 39-40, wherein the reinforcing member is radially inset from the lateral edges of the upper and lower tabs of the first and second leaflets.

Example 42. The prosthetic heart valve of any example herein, particularly any one of examples 39-41, wherein the plurality of loops extend through the first and second end portions of the reinforcing member.

Example 43. The prosthetic heart valve of any example herein, particularly any one of examples 39-42, the commissure member comprising a first end portion and a second end portion, wherein the commissure member is folded such that the first and second end portions are disposed adjacent one another.

Example 44. The prosthetic heart valve of any example herein, particularly any one of examples 39-43, wherein first and second lateral edges of the commissure member do not extend past first and second lateral edges of the upper and lower tabs of the first and second leaflets.

Example 45. The prosthetic heart valve of any example herein, particularly any one of examples 39-44, wherein the reinforcing member, the upper and lower tabs of the first and second leaflets, and the commissure member are coupled together via one or more fastening sutures.

Example 46. The prosthetic heart valve of any example herein, particularly example 45, wherein the fastening sutures extend through the first end portion and the second end portion of the reinforcing member.

Example 47. The prosthetic heart valve of any example herein, particularly any one of examples 39-46, wherein the plurality of loops extend through the reinforcing member.

Example 48. The prosthetic heart valve of any example herein, particularly any one of examples 39-47, wherein the plurality of loops extend through the lateral edges of the upper and lower tabs of the first and second leaflets.

Example 49. The prosthetic heart valve of any example herein, particularly any one of examples 39-48, further comprising one or more additional sutures sewn through a central portion of the commissure member to bias the upper and lower tabs of the first leaflet away from the upper and lower tabs of the second leaflet.

Example 50. The prosthetic heart valve of any example herein, particularly any one of examples 39-49, wherein the integral upper and lower tabs of each leaflet are first integral upper and lower tabs, and wherein each leaflet further comprises second integral upper and lower tabs arranged at an opposing end of a cusp edge portion of the leaflet.

Example 51. The prosthetic heart valve of any example herein, particularly any one of examples 39-50, wherein the reinforcing member comprises at least one of multi-filament suture, braided cloth, metallic braid, and metal strip.

Example 52. The prosthetic heart valve of any example herein, particularly any one of examples 39-51, wherein the reinforcing member comprises an Ethibond suture.

Example 53. The prosthetic heart valve of any example herein, particularly any one of examples 39-52, wherein the commissure member comprises PET.

Example 54. The prosthetic heart valve of any example herein, particularly any one of examples 39-53, wherein the reinforcing member is radially inset from lateral edges of the upper and lower tabs of the first and second leaflets.

Example 55. The prosthetic heart valve of any example herein, particularly any one of examples 39-54, wherein the valvular structure comprises three leaflets, each leaflet coupled one or more adjacent leaflets at a respective commissure.

Example 56. A prosthetic heart valve, comprising:
a radially expandable and compressible annular frame comprising a plurality of commissure features;
a valvular structure comprising a plurality of commissures, each commissure comprising:
a first leaflet having an integral upper tab and an integral lower tab, the upper tab being folded over the lower tab,
a second leaflet having an integral upper tab and an integral lower tab, the upper tab being folded over the lower tab,
a commissure member disposed between the lower tabs of the first and second leaflets;
a reinforcing member having a first end portion disposed on the upper tab of the first leaflet and a second end portion disposed on the upper tab of the second leaflet; and
wherein each commissure is coupled to a respective commissure feature via a plurality of loops coupled to the commissure and extending around the commissure feature, such that the valvular structure is disposed within and supported by the frame.

Example 57. The prosthetic heart valve of any example herein, particularly example 56, wherein the integral upper and lower tabs of the first leaflet are first integral upper and lower tabs, and wherein the first leaflet further comprises second integral upper and lower tabs arranged at an opposing end of a cusp edge portion of the leaflet.

Example 58. The prosthetic heart valve of any example herein, particularly any one of examples 56-57, wherein the reinforcing member is radially inset from the lateral edges of the upper and lower tabs of the first and second leaflets.

Example 59. The prosthetic heart valve of any example herein, particularly any one of examples 56-58, wherein the plurality of loops extend through the first and second end portions of the reinforcing member.

Example 60. The prosthetic heart valve of any example herein, particularly any one of examples 56-59, the commissure member comprising a first end portion and a second end portion, wherein the commissure member is folded such that the first and second end portions are disposed adjacent one another.

Example 61. The prosthetic heart valve of any example herein, particularly any one of examples 56-60, wherein first and second lateral edges of the commissure member do not extend past first and second lateral edges of the upper and lower tabs of the first and second leaflets.

Example 62. The prosthetic heart valve of any example herein, particularly any one of examples 56-61, wherein the reinforcing member, the upper and lower tabs of the first and second leaflets, and the commissure member are coupled together via one or more fastening sutures.

Example 63. The prosthetic heart valve of any example herein, particularly example 62, wherein the fastening sutures extend through the first end portion and the second end portion of the reinforcing member.

Example 64. The prosthetic heart valve of any example herein, particularly any one of examples 56-63, wherein the plurality of loops extend through the reinforcing member.

Example 65. The prosthetic heart valve of any example herein, particularly any one of examples 56-64, wherein the plurality of loops extend through the lateral edges of the upper and lower tabs of the first and second leaflets.

Example 66. The prosthetic heart valve of any example herein, particularly any one of examples 56-65, further comprising one or more additional sutures sewn through a central portion of the commissure member to bias the upper and lower tabs of the first leaflet away from the upper and lower tabs of the second leaflet.

Example 67. The prosthetic heart valve of any example herein, particularly example 66, wherein one or more stitches of the additional sutures wrap around an inflow edge of the upper and lower tabs.

Example 68. The prosthetic heart valve of any example herein, particularly any one of examples 56-67, wherein the integral upper and lower tabs of each leaflet are first integral upper and lower tabs, and wherein each leaflet further comprises second integral upper and lower tabs arranged at an opposing end of a cusp edge portion of the leaflet.

Example 69. The prosthetic heart valve of any example herein, particularly any one of examples 56-68, wherein the reinforcing member comprises at least one of multi-filament suture, braided cloth, metallic braid, and metal strip.

Example 70. The prosthetic heart valve of any example herein, particularly any one of examples 56-69, wherein the reinforcing member comprises an Ethibond suture.

Example 71. The prosthetic heart valve of any example herein, particularly any one of examples 56-70, wherein the commissure member comprises PET.

Example 72. The prosthetic heart valve of any example herein, particularly any one of examples 56-71, wherein the reinforcing member is radially inset from lateral edges of the upper and lower tabs of the first and second leaflets.

Example 73. The prosthetic heart valve of any example herein, particularly any one of examples 56-72, wherein the valvular structure comprises three leaflets, each leaflet coupled one or more adjacent leaflets at a respective commissure.

The invention claimed is:

1. A method of assembling a valvular structure, comprising:

folding an integral upper tab of a first leaflet onto an integral lower tab of the first leaflet such that a first surface of the upper tab contacts a first surface of the lower tab;

disposing a first end portion of a reinforcing member on a second surface of the upper tab of the first leaflet;

disposing a commissure member adjacent a second surface of the lower tab of the first leaflet;

coupling the first end portion of the reinforcing member, the upper and lower tabs of the first leaflet, and the commissure member to one another using one or more fastening sutures;

folding an integral upper tab of a second leaflet onto an integral lower tab of the second leaflet such that a first surface of the upper tab contacts a first surface of the lower tab;

disposing the second leaflet adjacent the first leaflet such that the commissure member is positioned between the respective lower tabs;

disposing a second end portion of the reinforcing member on a second surface of the upper tab of the second leaflet; and coupling the second end portion of the reinforcing member, the upper and lower tabs of the second leaflet, and the commissure member to one another using the one or more fastening sutures to form a commissure.

2. The method of claim 1, further comprising:

prior to disposing the second leaflet adjacent the first leaflet, folding the commissure member such that first and second lateral edges of the commissure member are disposed adjacent one another.

3. The method of claim 2, further comprising:

cutting back the first and second lateral edges of the commissure member such that they do not extend past lateral edges of the upper and lower tabs of the first and second leaflets.

4. The method of claim 1, wherein the one or more fastening sutures extend through the first end portion and the second end portion of the reinforcing member.

5. The method of claim 1, wherein the commissure member comprises first and second layers.

6. The method of claim 1, further comprising:

sewing one or more securing sutures through the commissure such that they extend around the lateral edges of the upper and lower tabs of the first and second leaflets to form a plurality of loops;

sliding the plurality of loops axially over a commissure support portion of an expansion and locking mechanism coupled to a frame of a prosthetic heart valve such that the leaflets are disposed within the frame; and tightening the plurality of loops to secure the leaflets to the frame.

7. The method of claim 6, wherein sewing one or more securing sutures through the commissure comprises sewing the securing sutures through the reinforcing member.

8. The method of claim 6, wherein sewing one or more securing sutures through the commissure comprises sewing the securing sutures through the lateral edges of the upper and lower tabs of the first and second leaflets.

9. The method of claim 1, further comprising sewing one or more additional sutures through the commissure member to bias the upper and lower tabs of the first and second leaflets away from one another.

10. The method of claim 1, wherein the integral upper and lower tabs of each leaflet are first integral upper and lower tabs, and wherein each leaflet further comprises second integral upper and lower tabs arranged at an opposing end of a cusp edge portion of the leaflet.

11. The method of claim 1, wherein the reinforcing member comprises at least one of multi-filament suture, braided cloth, metallic braid, and metal strip.

12. The method of claim 1, wherein the reinforcing member comprises an Ethibond suture.

13. The method of claim 1, wherein the commissure member comprises PET.

14. The method of claim 1, wherein the reinforcing member is radially inset from the lateral edges of the upper and lower tabs of the first and second leaflets.

* * * * *